(12) United States Patent
Shia et al.

(10) Patent No.: US 7,803,799 B2
(45) Date of Patent: Sep. 28, 2010

(54) SELENOPHENE COMPOUNDS

(75) Inventors: Kak-Shan Shia, Taipei (TW); Jing-Po Tsao, Hsinchu (TW); Chia-Liang Tai, Hsinchu (TW); Wan-Ping Hsieh, Taoyuan (TW); Ming-Shiu Hung, Taoyuan (TW); Jen-Shin Song, Taipei (TW); Yu-Sheng Chao, Warren, NJ (US)

(73) Assignee: National Health Research Institutes, Miaoli County (TW)

( * ) Notice: Subject to any disclaimer, the term of this patent is extended or adjusted under 35 U.S.C. 154(b) by 385 days.

(21) Appl. No.: 11/773,089

(22) Filed: Jul. 3, 2007

(65) Prior Publication Data

US 2008/0021031 A1 Jan. 24, 2008

Related U.S. Application Data

(60) Provisional application No. 60/819,147, filed on Jul. 7, 2006.

(51) Int. Cl.
*A61K 31/4155* (2006.01)
*A61K 31/454* (2006.01)
*A61K 31/4725* (2006.01)
*A61P 11/00* (2006.01)
*C07D 421/04* (2006.01)
*C07D 421/14* (2006.01)

(52) U.S. Cl. .................... 514/236.5; 514/307; 514/326; 514/406; 544/140; 546/146; 546/211; 548/364.7; 548/365.7

(58) Field of Classification Search ........................ None
See application file for complete search history.

(56) References Cited

U.S. PATENT DOCUMENTS

| | | | |
|---|---|---|---|
| 5,624,941 | A | 4/1997 | Barth et al. |
| 6,620,804 | B2 | 9/2003 | Chang et al. |
| 6,958,339 | B2 | 10/2005 | Kubota et al. |
| 2001/0011090 | A1 | 8/2001 | Kubota et al. |
| 2005/0261281 | A1 | 11/2005 | Lazzari et al. |

FOREIGN PATENT DOCUMENTS

| | | |
|---|---|---|
| EP | 1623741 | 2/2006 |
| JP | 2053787 | 2/1990 |

OTHER PUBLICATIONS

Tseng et al., "Bioisosteric Replacement of the Pyrazile 5-Aryl Moiety of N-(Piperidin-1-yl)-5-(4-chlorophenyl)-1-(2,4-dichlorophenyl)-4-methyl-1H-pyrazole-3-caroxamide (SR141716A). A Novel Series of Alkynylthiophenes as Potent and Selective Cannabinoid-1 Receptor Antagonists," J. Med. Chem., 51:5397-5412 (2008).
Obata et al., caplus an, 1994:700884.
Morimoto et al., caplus an 1970:456092.
Finar, "Preparation and Properties of Some Bipyrazolyls," Journal of the Chemical Society, pp. 12288, (1956) (Abstract).
Clark et al., "Decreased Incidence of Prostate Cancer with Selenium Supplementation: Results of a Double-Blind Cancer Prevention Trial," British Journal of Urology, 81:730-734 (1998).
Clark et al., "Effects of Selenium Supplementation for Cancer Prevention in Patients with Carcinoma of the Skin," JAMA, 276:1957-1963 (1996).
Diwadkar-Navsariwala et al., "Selenoprotein Deficiency Accelerates Prostate Carcingenesis in a Transgenic Model," PNAS, 103(21):8179-8184 (2006).
Database CAS Online on STN, Chem. Abst., Accession No. 2005:1242633, US 20050261281 A1 (Lazzari et al.) Nov. 24, 2005; abstract.

*Primary Examiner*—Kamal A Saeed
(74) *Attorney, Agent, or Firm*—Occhiuti Rohlicek & Tsao LLP

(57) ABSTRACT

This invention relates to selenophene compounds of formula (I) shown below. Each variable in formula (I) is defined in the specification. These compounds can be used to treat cannabinoid-receptor mediated disorders.

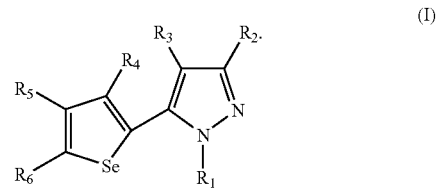

(I)

10 Claims, No Drawings

SELENOPHENE COMPOUNDS

CROSS-REFERENCE TO RELATED APPLICATIONS

This application claims the benefit under 35 USC 119(e) from U.S. Provisional Application No. 60/819,147, filed Jul. 7, 2006.

BACKGROUND

Cannabinoids isolated from *Cannabis sativa* have been recognized for centuries as therapeutic agents. For example, they have been utilized in treating analgesia, muscle relaxation, appetite stimulation, and anti-convulsion. Recent studies also indicate their potential therapeutic effects in treating cancer and alleviating the symptoms of chronic inflammatory diseases, such as rheumatism and multiple sclerosis.

The actions of cannabinoids are mediated by at least two types of the cannabinoid receptors, CB1 and CB2 receptors, both of which belong to the G-protein-coupled receptor (GPCR) superfamily. CB1 receptor is predominantly expressed in brain to mediate inhibition of transmitter release and CB2 receptor is primarily expressed in immune cells to modulate immune response. See Matsuda et al., *Nature* (1990) 346:561 and Munro et al., *Nature* (1993) 365:61.

Compared to other GPCRs, CB1 receptor is typically expressed at a higher level. In the central nervous system, it is highly expressed in cerebral cortex, hippocampus, basal ganglia, and cerebellum, but has a relatively low level in hypothalamus and spinal cord. See, e.g., Howlett et al., *Pharmacol Rev* (2002) 54:161. Its functions affect many neurological and psychological phenomena, such as mood, appetite, emesis control, memory, spatial coordination muscle tone, and analgesia. See, e.g., Goutopoulos et al., *Pharmacol Ther* (2002) 95:103. Other than the central nervous system, it is also present in several peripheral organs, such as gut, heart, lung, uterus, ovary, testis, and tonsils. See, e.g., Galiegue et al., *Eur J Biochem* (1995) 232:54.

CB2 receptor is 44% identical to CB1 receptor with a 68% identity in the trans-membrane regions. See Munro et al., *Nature* (1993) 365:61. Compared to CB1 receptor, CB2 receptor has a more limited distribution with a high expression in spleen and tonsils, but a low expression in lung, uterus, pancreas, bone marrow, and thymus. Among immune cells, B cells express CB2 receptor at the highest level, followed in order by natural killer cells, monocytes, polymorphonuclear neutrophils, and T lymphocytes. See Galiègue et al., *Eur J Biochem* (1995) 232:54. Activation of CB2 receptor has been shown to have analgesic effects in inflammatory models involved in neurodegeneration diseases (such as Alzheimer's disease), and also play a role in the maintenance of bone density and the progression of atherosclerotic lesions. See, e.g., Malan et al., *Pain* (2001) 93:239; Benito et al., *J Neurosci* (2003) 23:11136; Ibrahim et al., *Proc Natl Acad Sci USA* (2003) 100:10529; Idris et al., *Nat Med* (2005) 11:774; and Steffens et al., *Nature* (2005) 434:782.

SUMMARY

This invention is based on the discovery that certain selenophene compounds are effective in treating cannabinoid-receptor mediated disorders.

In one aspect, this invention features selenophene compounds of formula (I):

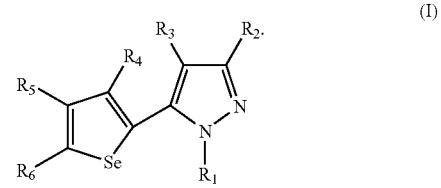

In this formula, $R_1$ is H, $C_1$-$C_{10}$ alkyl, $C_2$-$C_{10}$ alkenyl, $C_2$-$C_{10}$ alkynyl, $C_3$-$C_{20}$ cycloalkyl, $C_3$-$C_{20}$ cycloalkenyl, $C_1$-$C_{20}$ heterocycloalkyl, $C_1$-$C_{20}$ heterocycloalkenyl, aryl, or heteroaryl; $R_2$ is H, $C_1$-$C_{10}$ alkyl, $C_2$-$C_{10}$ alkenyl, $C_2$-$C_{10}$ alkynyl, $C_3$-$C_{20}$ cycloalkyl, $C_3$-$C_{20}$ cycloalkenyl, $C_1$-$C_{20}$ heterocycloalkyl, $C_1$-$C_{20}$ heterocycloalkenyl, aryl, heteroaryl, halo, $OR_a$, $COOR_a$, $OC(O)R_a$, $C(O)R_a$, $C(O)NR_aR_b$, or $NR_aR_b$, in which each of $R_a$ and $R_b$, independently, is H, $C_1$-$C_{10}$ alkyl, $C_3$-$C_{20}$ cycloalkyl, $C_1$-$C_{20}$ heterocycloalkyl, aryl, or heteroaryl; and each of $R_3$, $R_4$, $R_5$, and $R_6$, independently, is H, halo, $C_1$-$C_{10}$ alkyl, $C_2$-$C_{10}$ alkenyl, $C_2$-$C_{10}$ alkynyl, $C_3$-$C_{20}$ cycloalkyl, $C_3$-$C_{20}$ cycloalkenyl, $C_1$-$C_{20}$ heterocycloalkyl, $C_1$-$C_{20}$ heterocycloalkenyl, aryl, or heteroaryl.

Referring to formula (I), a subset of the selenophene compounds described above are those in which $R_1$ is aryl substituted with halo (e.g., 2,4-dichlorophenyl). In these compounds, $R_2$ can be $C(O)NR_aR_b$, $C(O)R_a$, or $C_1$-$C_{10}$ alkyl substituted with $C_1$-$C_{20}$ heterocycloalkyl, $NHC(O)NR_cR_d$, $NHC(S)NR_cR_d$, or $NHC(O)R_c$, in which $R_c$ and $R_d$, independently, is H, $C_1$-$C_{10}$ alkyl, $C_3$-$C_{20}$ cycloalkyl, $C_1$-$C_{20}$ heterocycloalkyl, aryl, or heteroaryl. As one example, $R_2$ can be $C(O)NR_aR_b$, in which $R_a$ is methyl substituted with 6,6-dimethylbicyclo[3.1.1]heptyl, ethyl substituted with admantyl or cyclohexenyl, hexyl, nonyl, cyclopentyl, cyclohexyl, cycloheptyl, pyridyl, morpholinyl, octahydrocyclopentapyrrolyl, or tetrahydronaphthyl; and $R_b$ is H. As another example, $R_2$ can be $C(O)R_a$, in which $R_a$ is pyridyl, tetrahydroquinolinyl, decahydroquinolinyl, or methyl substituted with C(O)R or C(O)NRR'; R being ethyl, isobutyl, pyrrolidinyl, or pyridyl optionally substituted with methyl, and R' being ethyl or isobutyl. As another example, $R_2$ can be $C_1$-$C_{10}$ alkyl substituted with 1-methylimidazolidinone, 1-cyclohexylimidazolidinone, 1-phenylimidazolidinone, $NHC(O)NR_cR_d$, $NHC(S)NR_cR_d$, or $NHC(O)R_c$, in which $R_c$ is propyl, cyclopropyl, cyclobutyl, cyclopentyl, cyclohexyl, cycloheptyl, cyclooctyl, or phenyl and $R_d$ is H.

The term "alkyl" refers to a saturated, linear or branched hydrocarbon moiety, such as —$CH_3$ or —$CH(CH_3)_2$. The term "alkenyl" refers to a linear or branched hydrocarbon moiety that contains at least one double bond, such as —CH=CH—$CH_3$. The term "alkynyl" refers to a linear or branched hydrocarbon moiety that contains at least one triple bond, such as —C≡C—$CH_3$. The term "cycloalkyl" refers to a saturated, cyclic hydrocarbon moiety, such as cyclohexyl. The term "cycloalkenyl" refers to a non-aromatic, cyclic hydrocarbon moiety that contains at least one double bond, such as cyclohexenyl. The term "heterocycloalkyl" refers to a saturated, cyclic moiety having at least one ring heteroatom (e.g., N, O, or S), such as 4-tetrahydropyranyl. The term "heterocycloalkenyl" refers to a non-aromatic, cyclic moiety having at least one ring heteroatom (e.g., N, O, or S) and at least one double bond, such as pyranyl. The term "aryl" refers to a hydrocarbon moiety having one or more aromatic rings. Examples of aryl moieties include phenyl (Ph), phenylene, naphthyl, naphthylene, pyrenyl, anthryl, and phenanthryl. The term "heteroaryl" refers to a moiety having one or more aromatic rings that contain at least one heteroatom (e.g., N, O, or S). Examples of heteroaryl moieties include furyl, furylene, fluorenyl, pyrrolyl, thienyl, oxazolyl, imidazolyl, thiazolyl, pyridyl, pyrimidinyl, quinazolinyl, quinolyl, isoquinolyl and indolyl.

Alkyl, alkenyl, alkynyl, cycloalkyl, cycloalkenyl, heterocycloalkyl, heterocycloalkenyl, aryl, and heteroaryl mentioned herein include both substituted and unsubstituted moieties, unless specified otherwise. Possible substituents on cycloalkyl, cycloalkenyl, heterocycloalkyl, heterocycloalkenyl, aryl, and heteroaryl include, but are not limited to, $C_1$-$C_{10}$ alkyl, $C_2$-$C_{10}$ alkenyl, $C_2$-$C_{10}$ alkynyl, $C_3$-$C_{20}$ cycloalkyl, $C_3$-$C_{20}$ cycloalkenyl, $C_1$-$C_{20}$ heterocycloalkyl, $C_1$-$C_{20}$ heterocycloalkenyl, $C_1$-$C_{10}$ alkoxy, aryl, aryloxy, heteroaryl, heteroaryloxy, amino, $C_1$-$C_{10}$ alkylamino, $C_1$-$C_{20}$ dialkylamino, arylamino, diarylamino, hydroxyl, halo, thio, $C_1$-$C_{10}$ alkylthio, arylthio, $C_1$-$C_{10}$ alkylsulfonyl, arylsulfonyl, acylamino, aminoacyl, aminothioacyl, amidino, guanidine, ureido, cyano, nitro, acyl, thioacyl, acyloxy, carboxyl, and carboxylic ester. On the other hand, possible substituents on alkyl, alkenyl, or alkynyl include all of the above-recited substituents except $C_1$-$C_{10}$ alkyl. Cycloalkyl, cycloalkenyl, heterocycloalkyl, heterocycloalkenyl, aryl, and heteroaryl can also be fused with each other.

In another aspect, this invention features a method for treating a cannabinoid-receptor mediated disorder. The method includes administering to a subject in need thereof an effective amount of one or more selenophene compounds of formula (I) shown above. Examples of cannabinoid-receptor mediated disorders include hair loss, obesity, metabolic syndrome (e.g., syndrome X), hyperlipidemia, type II diabetes, atherosclerosis, substance addiction (e.g., alcohol addiction or nicotine addiction), depression, motivational deficiency syndrome, learning or memory dysfunction, analgesia, haemorrhagic shock, ischemia, liver cirrhosis, neuropathic pain, antiemesis, high intraocular pressure, bronchodilation, osteoporosis, cancer (e.g., prostate cancer, lung cancer, breast cancer, or head and neck cancer), a neurodegenerative disease (e.g., Alzheimer's disease or Parkinson's disease), or an inflammatory disease.

The term "treating" or "treatment" refers to administering one or more selenophene compounds to a subject, who has an above-described disorder, a symptom of such a disorder, or a predisposition toward such a disorder, with the purpose to confer a therapeutic effect, e.g., to cure, relieve, alter, affect, ameliorate, or prevent the above-described disorder, the symptom of it, or the predisposition toward it.

In addition, this invention encompasses a pharmaceutical composition that contains an effective amount of at least one of the above-mentioned selenophene compounds and a pharmaceutically acceptable carrier.

The selenophene compounds described above include the compounds themselves, as well as their salts, prodrugs, and solvates, if applicable. A salt, for example, can be formed between an anion and a positively charged group (e.g., amino) on a selenophene compound. Suitable anions include chloride, bromide, iodide, sulfate, nitrate, phosphate, citrate, methanesulfonate, trifluoroacetate, acetate, malate, tosylate, tartrate, fumurate, glutamate, glucuronate, lactate, glutarate, and maleate. Likewise, a salt can also be formed between a cation and a negatively charged group (e.g., carboxylate) on a selenophene compound. Suitable cations include sodium ion, potassium ion, magnesium ion, calcium ion, and an ammonium cation such as tetramethylammonium ion. The selenophene compounds also include those salts containing quaternary nitrogen atoms. Examples of prodrugs include esters and other pharmaceutically acceptable derivatives, which, upon administration to a subject, are capable of providing active selenophene compounds. A solvate refers to a complex formed between an active selenophene compound and a pharmaceutically acceptable solvent. Examples of pharmaceutically acceptable solvents include water, ethanol, isopropanol, ethyl acetate, acetic acid, and ethanolamine.

Also within the scope of this invention is a composition containing one or more of the selenophene compounds described above for use in treating an above-described disorder, and the use of such a composition for the manufacture of a medicament for the just-mentioned treatment.

The details of one or more embodiments of the invention are set forth in the description below. Other features, objects, and advantages of the invention will be apparent from the description and from the claims.

DETAILED DESCRIPTION

Shown below are 45 exemplary compounds of this invention:

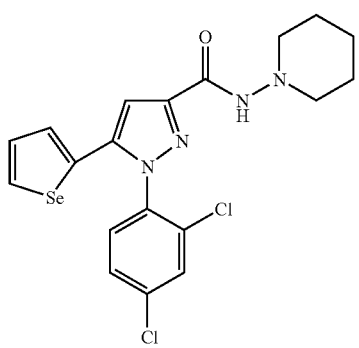

Compound 1

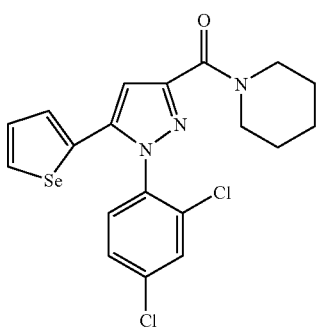

Compound 2

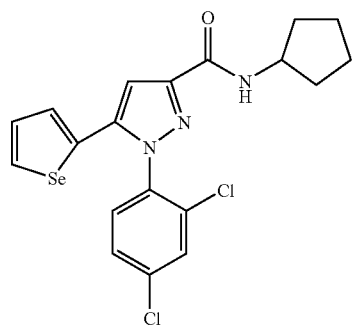

Compound 3

-continued
Compound 4
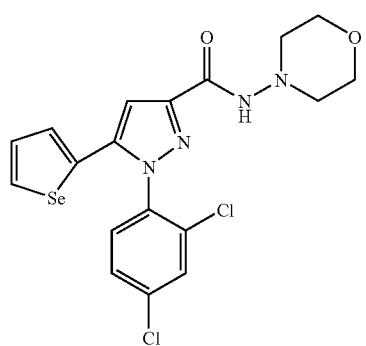
Compound 5
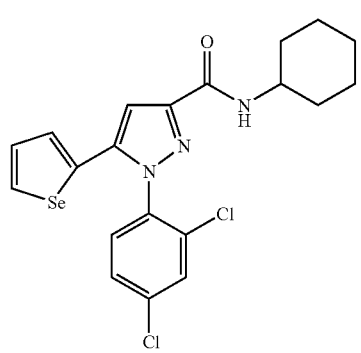
Compound 6
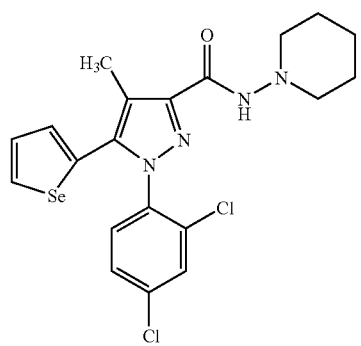
Compound 7
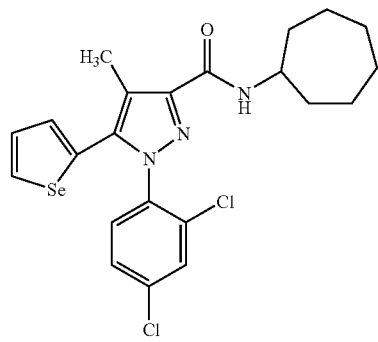
-continued
Compound 8
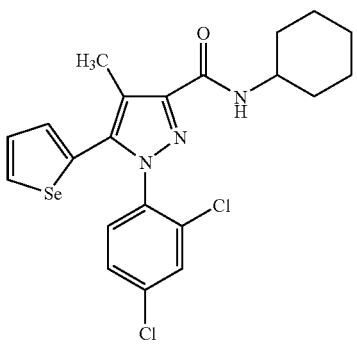
Compound 9
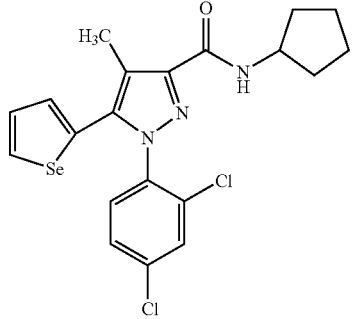
Compound 10
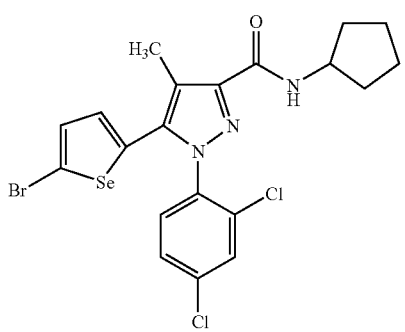
Compound 11
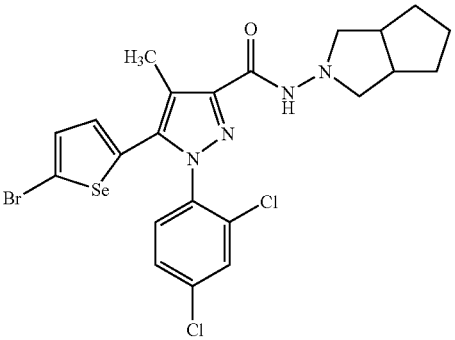

-continued
Compound 12
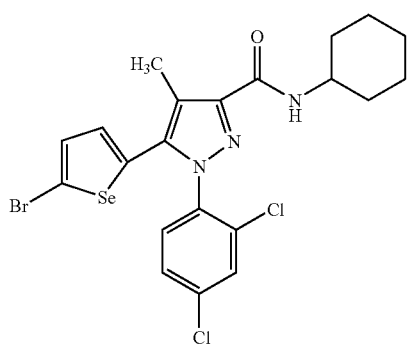
Compound 13
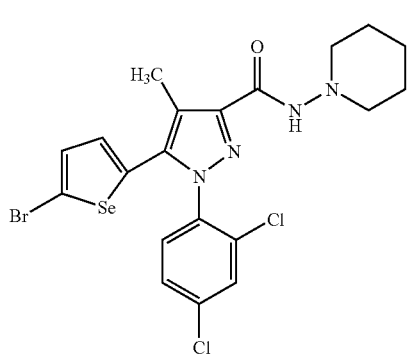
Compound 14
Compound 15
-continued
Compound 16
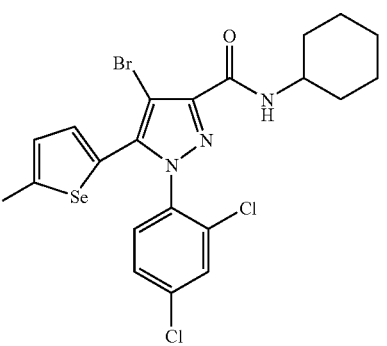
Compound 17
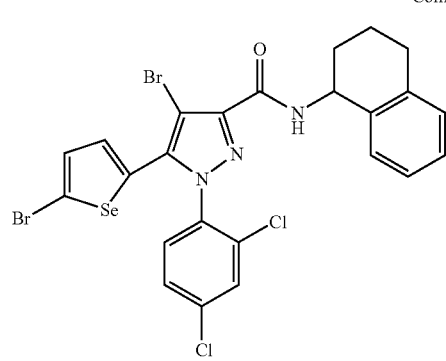
Compound 18
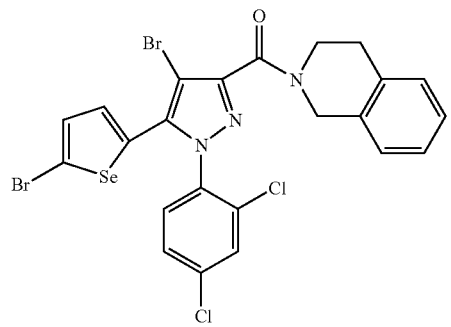
Compound 19
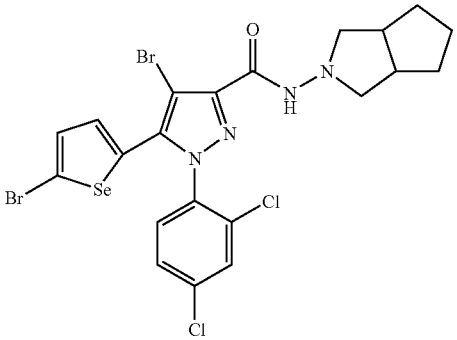

-continued
Compound 20
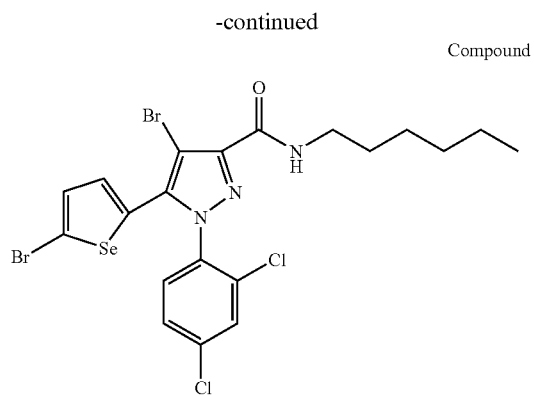
Compound 21
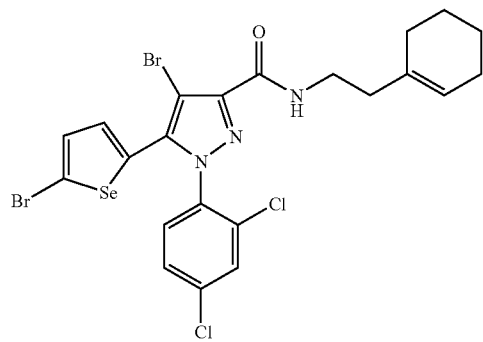
Compound 22
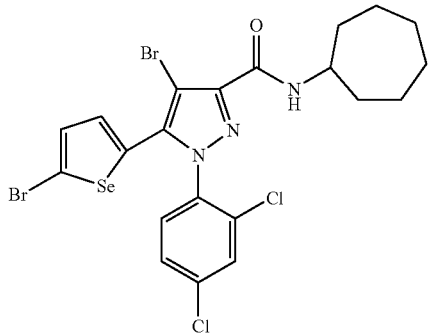
Compound 23
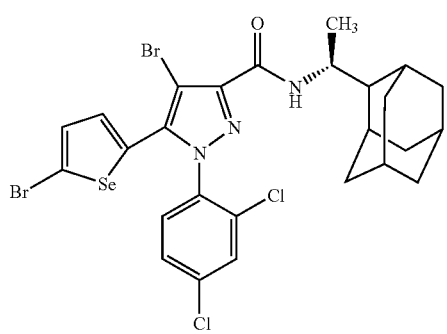
-continued
Compound 24
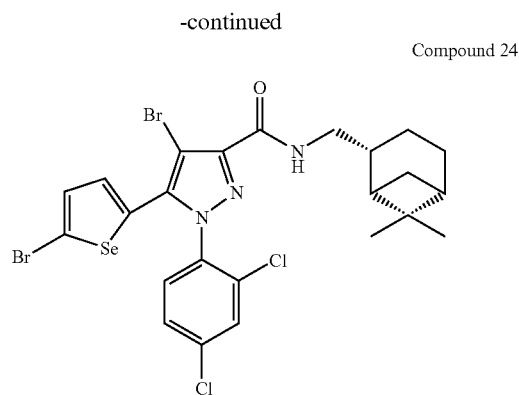
Compound 25
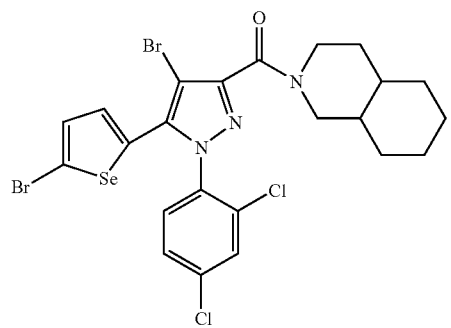
Compound 26
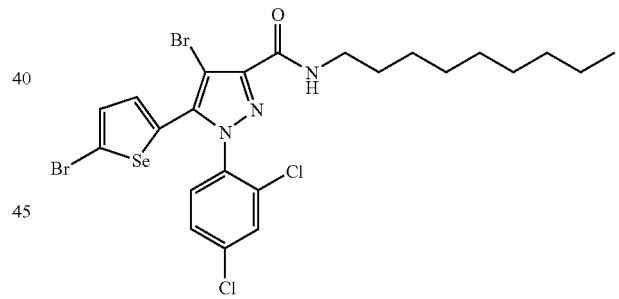
Compound 27
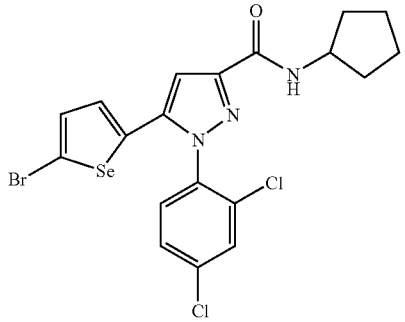

-continued
Compound 28
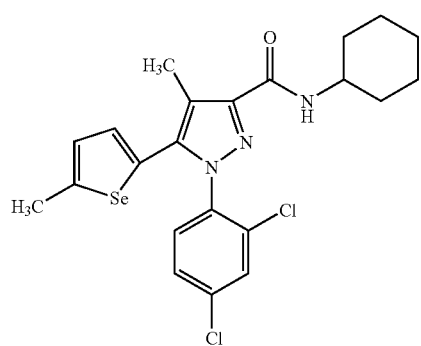
Compound 29
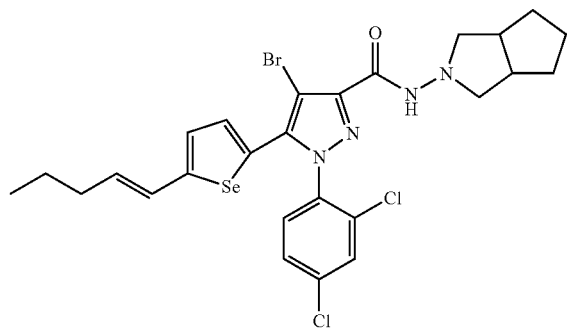
Compound 30
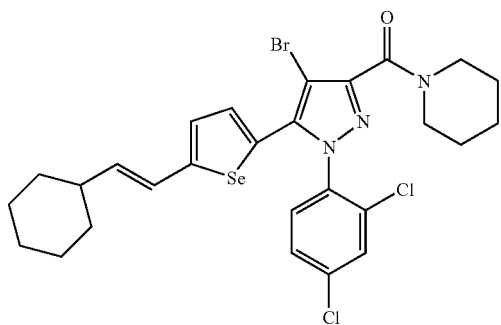
Compound 31
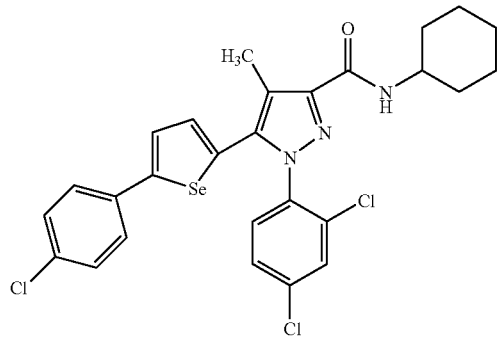
-continued
Compound 32
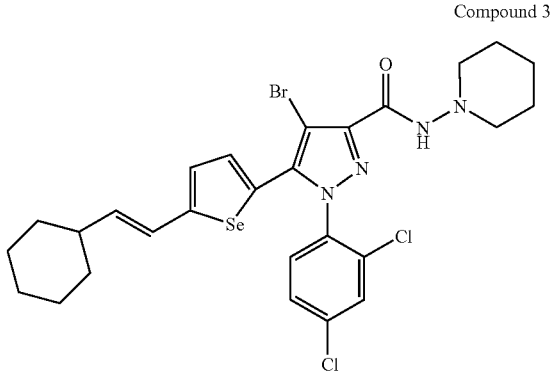
Compound 33
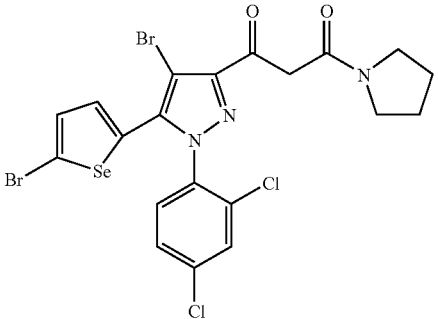
Compound 34
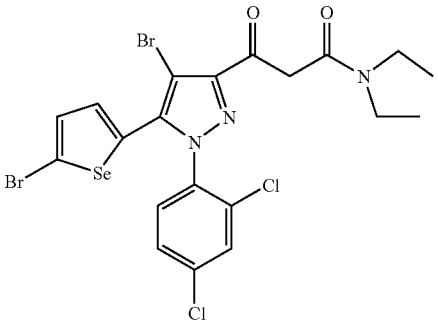
Compound 35

-continued
Compound 36
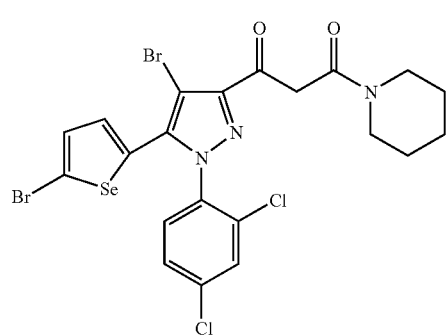
Compound 40
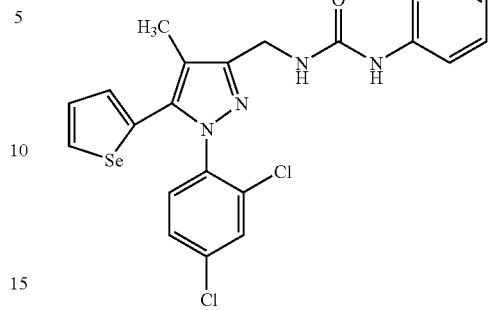
Compound 37
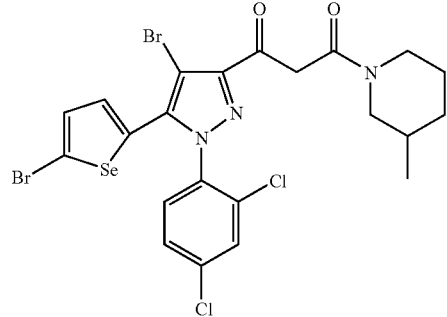
Compound 41
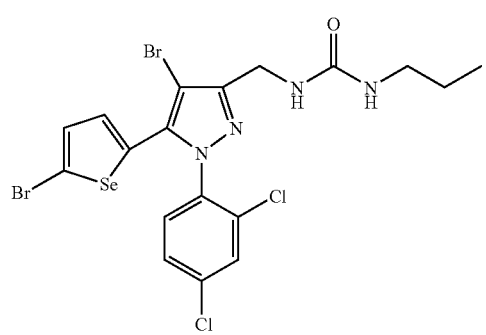
Compound 38
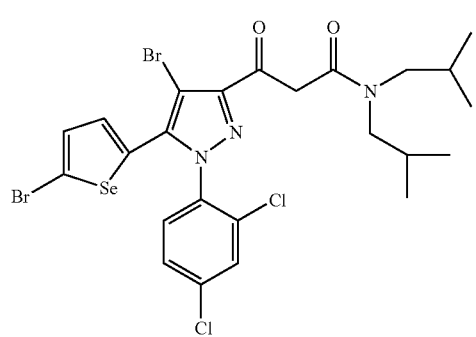
Compound 42
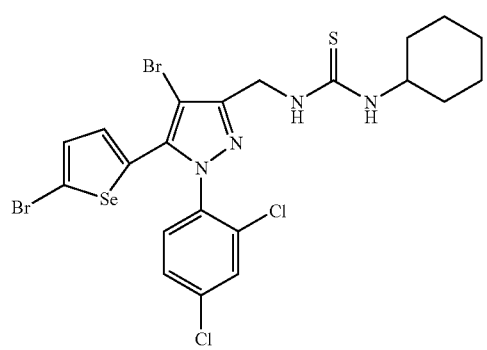
Compound 39
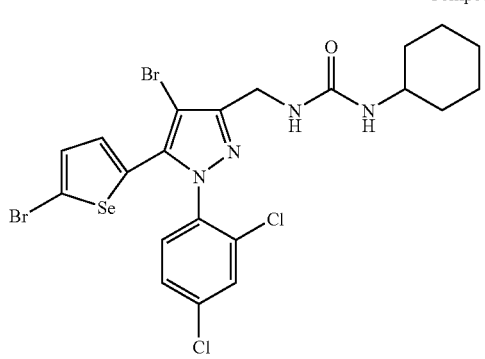
Compound 43
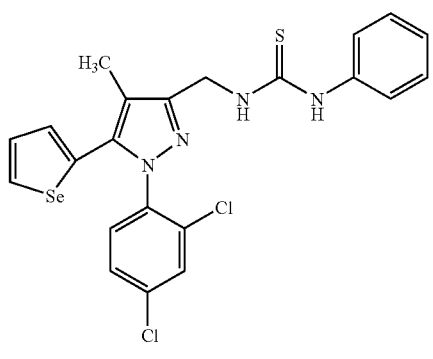

-continued

Compound 44

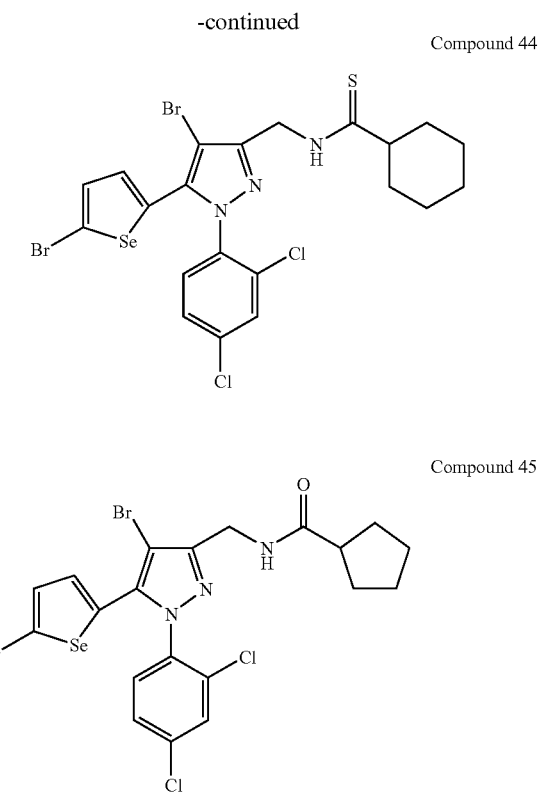

Compound 45

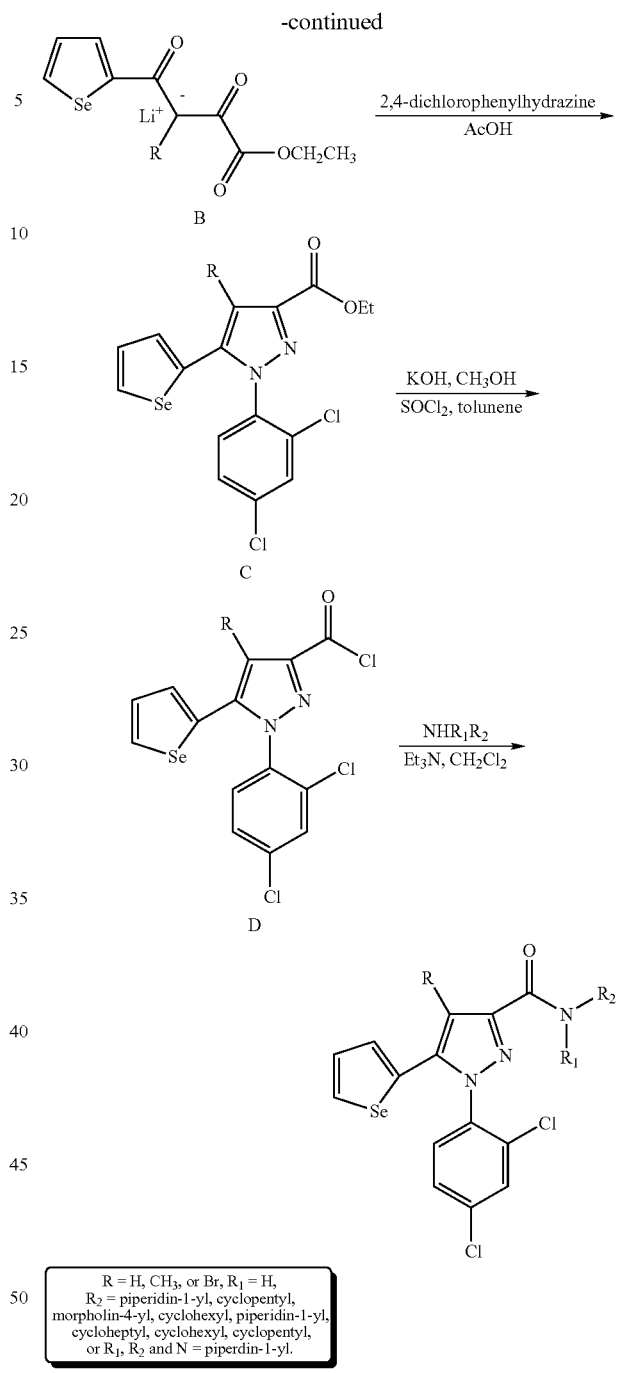

R = H, CH₃, or Br, R₁ = H,
R₂ = piperidin-1-yl, cyclopentyl,
morpholin-4-yl, cyclohexyl, piperidin-1-yl,
cycloheptyl, cyclohexyl, cyclopentyl,
or R₁, R₂ and N = piperdin-1-yl.

The selenophene compounds described above can be prepared by methods well known in the art. Examples 1-45 below provide detailed descriptions of the preparation of compounds 1-45.

Scheme I shown below depicts a typical synthetic route for synthesizing certain exemplary compounds. Specifically, a selenophene compound containing a ketone group (e.g., compound A) can first undergo a Claisen condensation reaction with an oxalate compound (e.g., diethyl oxalate) in the presence of a lithium salt to form a 1,3-dione compound containing an ester group (e.g., compound B). The 1,3-dione compound can then react with a hydrazine to afford a corresponding hydrazone, which, without purification, is allowed to undergo intramolecular cyclization under refluxing acetic acid to form a pyrazole compound (e.g., compound C) containing an ester group. The ester group on the pyrazole compound can be hydrolyzed in the presence of a base to form a carboxyl group, which in turn can be converted to an acyl chloride group by reacting with thionyl chloride. The compound thus formed (e.g., compound D) can then react with amine compounds to form certain compounds of the invention (e.g., compounds 1-9).

Scheme I

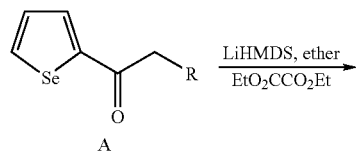

The pyrazole compound mentioned in Scheme I above can be modified in various manners to afford other compounds of this invention. For example, as shown in Scheme II below, the pyrazole compound can react with N-bromosuccinimide to form a compound containing a bromide group at the 5-position on the selenophene ring (e.g., compound E). This compound can then be hydrolyzed in the presence of a base to form a carboxyl group, which in turn can be converted to an acyl halide group by reacting with thionyl chloride. The compound thus formed (e.g., compound F) can either react with amine compounds to form certain compounds of the invention (e.g., compounds 10-27) or react with ketone compounds to form certain other compounds of the invention (e.g., compounds 34-38).

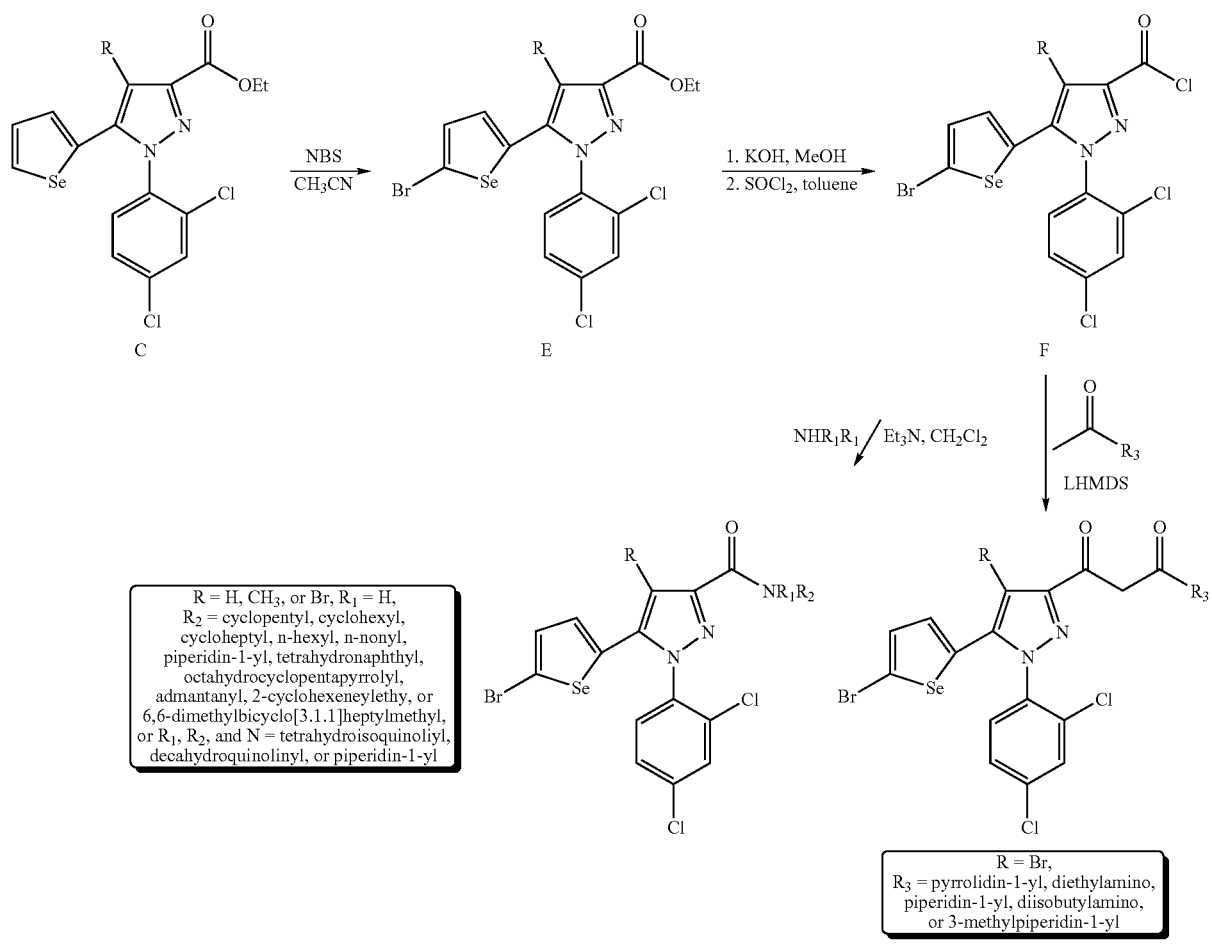

As shown in Scheme III below, the compound containing a bromide group at the 5-position on the selenophene ring (e.g., compound E) can also undergo a substitution reaction to replace the bromide group with other groups (e.g., an alkyl, alkenyl, or heterocycloalkyl group). The compound thus formed (e.g., compound G) can then be converted to a compound containing an acyl halide group (e.g., compound H) using the same method described above. The resultant compound can subsequently react with amine compounds to form certain compounds of the invention (e.g., compounds 28-33).

-continued

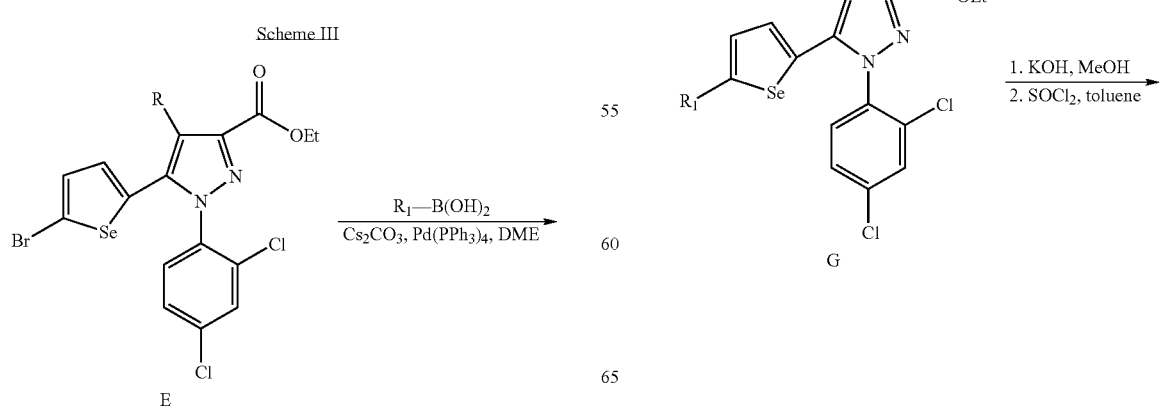

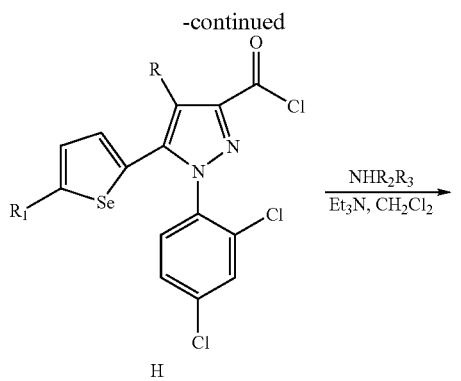

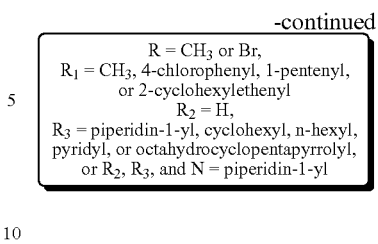

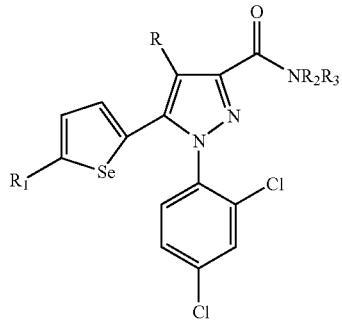

Alternatively, as shown in Scheme IV below, the compound containing a bromide group at the 5-position on the selenophene ring can be reduced to form a compound containing a hydroxyl group (e.g., compound I). The hydroxyl group can then be converted to a leaving group (e.g., by reacting with methanesulfonyl chloride). The compound thus formed (e.g., compound J) can first react with sodium azide and then triphenylphosphine to form an amine compound (e.g., compound K). The amine compound can either react with isocyanates or isothiocyanates to form certain compounds of the invention (e.g., compounds 39 and 42) or react with an acyl chloride to form certain other compounds of the invention (e.g., compounds 44 and 45).

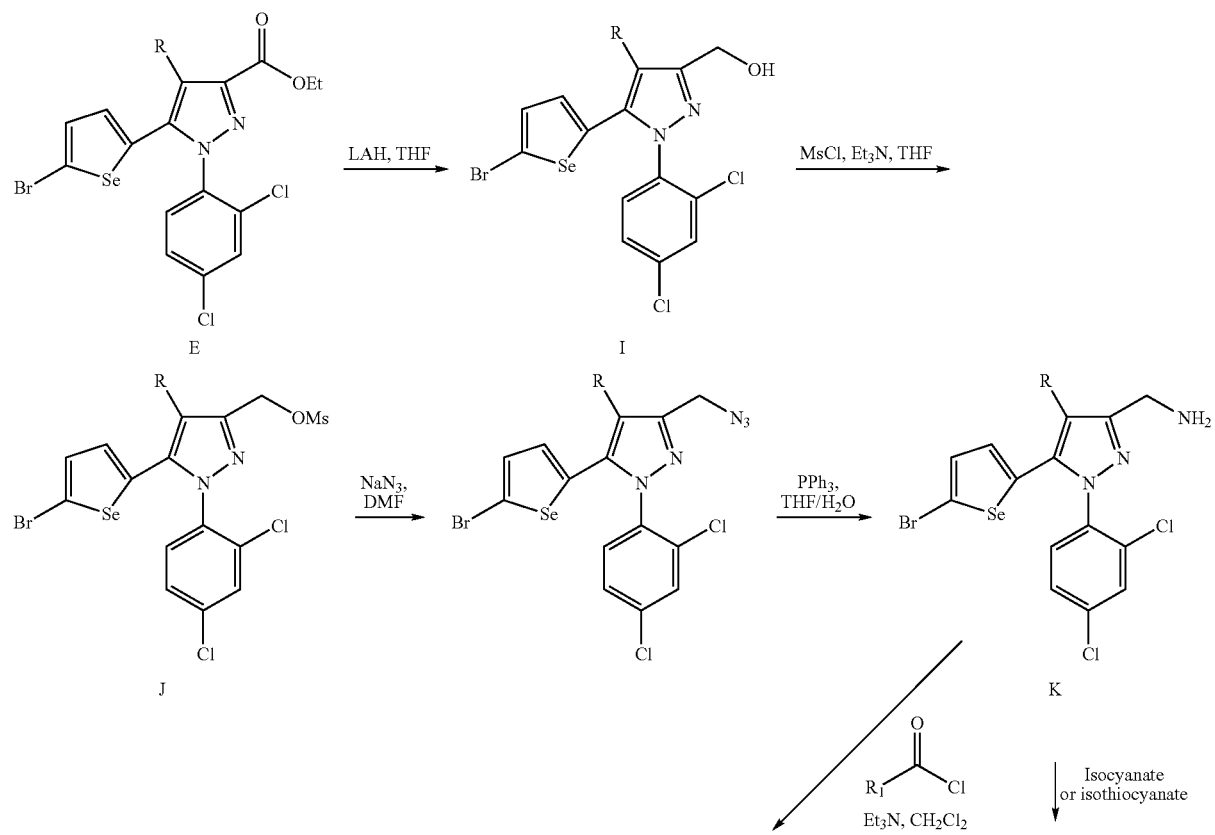

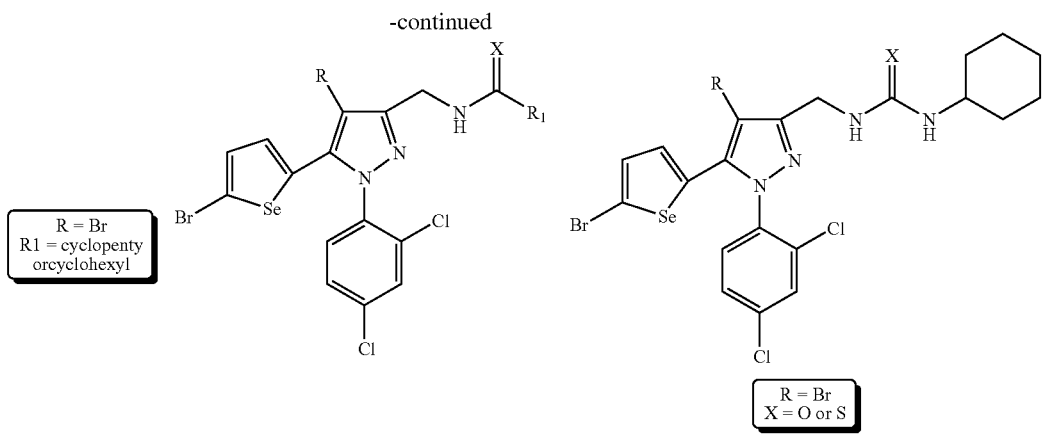

-continued

A selenophene compound synthesized above can be purified by a suitable method such as column chromatography, high-pressure liquid chromatography, or recrystallization.

Other selenophene compounds can be prepared using other suitable starting materials through the above synthetic routes and others known in the art. The methods described above may also additionally include steps, either before or after the steps described specifically herein, to add or remove suitable protecting groups in order to ultimately allow synthesis of the selenophene compounds. In addition, various synthetic steps may be performed in an alternate sequence or order to give the desired compounds. Synthetic chemistry transformations and protecting group methodologies (protection and deprotection) useful in synthesizing applicable selenophene compounds are known in the art and include, for example, those described in R. Larock, *Comprehensive Organic Transformations*, VCH Publishers (1989); T. W. Greene and P. G. M. Wuts, *Protective Groups in Organic Synthesis*, 2$^{nd}$ Ed., John Wiley and Sons (1991); L. Fieser and M. Fieser, *Fieser and Fieser's Reagents for Organic Synthesis*, John Wiley and Sons (1994); and L. Paquette, ed., *Encyclopedia of Reagents for Organic Synthesis*, John Wiley and Sons (1995) and subsequent editions thereof.

The selenophene compounds mentioned herein may contain a non-aromatic double bond and one or more asymmetric centers. Thus, they can occur as racemates and racemic mixtures, single enantiomers, individual diastereomers, diastereomeric mixtures, and cis- or trans-isomeric forms. All such isomeric forms are contemplated.

Also within the scope of this invention is a pharmaceutical composition containing an effective amount of at least one selenophene compound described above and a pharmaceutical acceptable carrier. Further, this invention covers a method of administering an effective amount of one or more of the selenophene compounds to a patient having a disease described in the summary section above. "An effective amount" refers to the amount of an active selenophene compound that is required to confer a therapeutic effect on the treated subject. Effective doses will vary, as recognized by those skilled in the art, depending on the types of diseases treated, route of administration, excipient usage, and the possibility of co-usage with other therapeutic treatment.

To practice the method of the present invention, a composition having one or more selenophene compounds can be administered parenterally, orally, nasally, rectally, topically, or buccally. The term "parenteral" as used herein refers to subcutaneous, intracutaneous, intravenous, intramuscular, intraarticular, intraarterial, intrasynovial, intrasternal, intrathecal, intralesional, or intracranial injection, as well as any suitable infusion technique.

A sterile injectable composition can be a solution or suspension in a non-toxic parenterally acceptable diluent or solvent, such as a solution in 1,3-butanediol. Among the acceptable vehicles and solvents that can be employed are mannitol, water, Ringer's solution, and isotonic sodium chloride solution. In addition, fixed oils are conventionally employed as a solvent or suspending medium (e.g., synthetic mono- or diglycerides). Fatty acid, such as oleic acid and its glyceride derivatives are useful in the preparation of injectables, as are natural pharmaceutically acceptable oils, such as olive oil or castor oil, especially in their polyoxyethylated versions. These oil solutions or suspensions can also contain a long chain alcohol diluent or dispersant, carboxymethyl cellulose, or similar dispersing agents. Other commonly used surfactants such as Tweens or Spans or other similar emulsifying agents or bioavailability enhancers which are commonly used in the manufacture of pharmaceutically acceptable solid, liquid, or other dosage forms can also be used for the purpose of formulation.

A composition for oral administration can be any orally acceptable dosage form including capsules, tablets, emulsions and aqueous suspensions, dispersions, and solutions. In the case of tablets, commonly used carriers include lactose and corn starch. Lubricating agents, such as magnesium stearate, are also typically added. For oral administration in a capsule form, useful diluents include lactose and dried corn starch. When aqueous suspensions or emulsions are administered orally, the active ingredient can be suspended or dissolved in an oily phase combined with emulsifying or suspending agents. If desired, certain sweetening, flavoring, or coloring agents can be added.

A nasal aerosol or inhalation composition can be prepared according to techniques well known in the art of pharmaceutical formulation. For example, such a composition can be prepared as a solution in saline, employing benzyl alcohol or other suitable preservatives, absorption promoters to enhance bioavailability, fluorocarbons, and/or other solubilizing or dispersing agents known in the art.

A composition having one or more active selenophene compounds can also be administered in the form of suppositories for rectal administration.

The carrier in the pharmaceutical composition must be "acceptable" in the sense that it is compatible with the active ingredient of the composition (and preferably, capable of stabilizing the active ingredient) and not deleterious to the subject to be treated. One or more solubilizing agents can be utilized as pharmaceutical excipients for delivery of an active selenophene compound. Examples of other carriers include colloidal silicon oxide, magnesium stearate, cellulose, sodium lauryl sulfate, and D&C Yellow # 10.

The selenophene compounds described above can be preliminarily screened for their efficacy in treating above-described diseases by an in vitro assay (See Example 46 below) and then confirmed by animal experiments and clinic trials. Other methods will also be apparent to those of ordinary skill in the art.

The specific examples below are to be construed as merely illustrative, and not limitative of the remainder of the disclosure in any way whatsoever. Without further elaboration, it is believed that one skilled in the art can, based on the description herein, utilize the present invention to its fullest extent. All publications cited herein are hereby incorporated by reference in their entirety.

EXAMPLE 1 Preparation of Compound 1

1-(2,4-dichlorophenyl)-N-(piperidin-1-yl)-5-(selenophen-2-yl)-1H-pyrazole-3-carboxamide A solution of 1-(selenophene-2-yl)ethanone (3.2 g, 18.49 mmol) in diethyl ether (13 mL) was added to a magnetically stirred solution of lithium bis(trimethylsilyl)amide (20.3 mL, 20.35 mmol) in diethyl ether (40 mL) at −78° C. After the mixture was stirred at the same temperature for additional 45 minutes, diethyl oxalate (3.0 mL, 22.19 mmol) was added. The reaction mixture was allowed to warm to room temperature and stirred for another 16 hours. The precipitate was filtered, washed with diethyl ether, and dried under vacuum to give Intermediate I(a), i.e., a lithium salt of ethyl 2,4-dioxo-4-(selenoehen-2-yl-butanonte) (3.5 g, 68%).

To a magnetically stirred solution of Intermediate I(a) (3.5 g, 12.56 mmol) in 40 mL of ethanol was added 2,4-dichlorophenylhydrazine hydrochloride (2.9 g, 13.82 mmol) in one portion at room temperature. The resultant mixture was stirred at room temperature for 20 hours. The precipitate thus formed was filtered, washed with ethanol and diethyl ether, and then dried under vacuum to give a light yellow solid (4.0 g, 74%). This solid was dissolved in acetic acid (30 mL) and heated under reflux for 24 hours. The reaction mixture was then poured into ice water and extracted with ethyl acetate. The combined extracts were washed sequentially with water, a saturated sodium bicarbonate aqueous solution, and brine. The organic layer was then separated, dried over anhydrous sodium sulfate, filtered, and concentrated to give a crude product, which was purified by flash column chromatography on silica gel with n-hexane/ethyl acetate (9:1) to give Intermediate II(a), i.e., 1-(2,4-dichlorophenyl)-5-selenophene-2-yl-1H-pyrazole-3-carboxylic acid ethyl ester, as a white solid (3.0 g, 78%).

A solution of potassium hydroxide (813 mg, 14.48 mmol) in methanol (7 mL) was added to a magnetically stirred solution of Intermediate II(a) (3.0 g, 7.24 mmol) in methanol (15 mL). The mixture was heated under reflux for 3 hours. The reaction mixture was cooled, poured into water, and acidified with a 10% hydrochloric acid aqueous solution. The precipitate was filtered, washed with water, and dried under vacuum to give Intermediate III(a), i.e., 1-(2,4-dichlorophenyl)-5-selenophene-2-yl-1H-pyrazole-3-carboxylic acid, as a white solid (2.6 g, 95%).

A solution of Intermediate III(a) (100 mg, 0.25 mmol) and thionyl chloride (67.1 µL, 0.92 mmol) in toluene (5 mL) was refluxed for 3 hours. The solvent was then evaporated under reduced pressure. The resultant residue was re-dissolved in toluene (5 mL) and evaporated again to yield a crude 1-(2,4-dichloro-phenyl)-5-selenophen-2-yl-1H-pyrazole-3-carboxylic chloride (100 mg, 96%) as a light solid. The carboxylic chloride dissolved in dichloromethane (5 mL) was added dropwise to a mixture of 1-aminopiperidine (42.7 µL, 0.39 mmol) and triethylamine (56.5 µL, 0.39 mmol) in 5 mL of dichloromethane at 0° C. After stirring at room temperature for 3 hours, the reaction was quenched with water. The aqueous layer was separated and extracted with dichloromethane (2×10 mL). The combined extracts were washed with brine, dried over anhydrous sodium sulfate, filtered, and concentrated to give a crude product, which was purified by flash column chromatography on silica gel with n-hexane/ethyl acetate (2:1) to give compound 1 as a white solid (86 mg, 75%).

$^1$H-NMR (CDCl$_3$, ppm): 7.96 (d, 1H), 7.56 (s, 1H), 7.46 (s, 2H), 7.21-7.12 (m, 3H), 6.80 (d, 1H), 4.43-4.36 (m, 1H), 2.10-2.01 (m, 2H), 1.74-1.47 (m, 6H).

ES-MS (M+1): 469.0.

EXAMPLE 2 Preparation of Compound 2

(1-(2,4-dichlorophenyl)-5-(selenophen-2-yl)-1H-pyrazol-3-yl)(piperidin-1-yl)methanone Compound 2 was prepared in a manner similar to that described in Example 1 except that, in the last step, the crude carboxylic chloride (100 mg, 0.24 mmol) was treated with piperidine.

$^1$H-NMR (CDCl$_3$, ppm): 7.95 (d, 1H), 7.55 (s, 1H), 7.42-7.33 (m, 2H), 7.21-7.12 (m, 3H), 6.93 (d, 1H), 3.87-3.72 (m, 4H), 1.74-1.46 (m, 6H).

ES-MS (M+1): 469.0.

EXAMPLE 3 Preparation of Compound 3

N-cyclopentyl-1-(2,4-dichlorophenyl)-5-(selenophen-2-yl)-1H-pyrazole-3-carboxamide Compound 3 was prepared in a manner similar to that described in Example 1 except that, in the last step, the crude carboxylic chloride (100 mg, 0.24 mmol) was treated with cyclopentyl amine (38.0 µL, 0.39 mmol) and triethylamine (56.5 µL, 0.39 mmol) to give compound 3 as a white solid (90 mg, 83%).

$^1$H-NMR (CDCl$_3$, ppm): 7.96 (d, 1H), 7.56 (s, 1H), 7.46 (brs, 2H), 7.21-7.12 (m, 2H), 6.80 (d, 1H), 4.43-4.36 (m, 1H), 2.10-2.02 (m, 2H), 1.74-1.47 (m, 6H).

ES-MS (M+23): 475.9.

EXAMPLE 4 Preparation of Compound 4

1-(2,4-dichlorophenyl)-N-morpholino-5-(selenophen-2-yl)-1H-pyrazole-3-carboxamide Compound 4 was prepared in a manner similar to that described in Example 1 except that, in the last step, the crude carboxylic chloride (100 mg, 0.24 mmol) was treated with N-aminomorpholine (37.9 µL, 0.39 mmol) and triethylamine (56.5 µL, 0.39 mmol) to give compound 4 as a white solid (79 mg, 70%).

$^1$H-NMR (CDCl$_3$, ppm): 7.98 (d, 1H), 7.62 (brs, 1H), 7.58 (d, 1H), 7.44 (brs, 2H), 7.22-7.13 (m, 3H), 3.87 (t, 2H), 2.94 (t, 2H)

ES-MS (M+1): 470.9.

EXAMPLE 5 Preparation of Compound 5

N-cyclohexyl-1-(2,4-dichlorophenyl)-5-(selenophen-2-yl)-1H-pyrazole-3-carboxamide Compound 5 was prepared in a manner similar to that described in Example 1 except that, in the last step, the crude carboxylic chloride (100 mg, 0.24 mmol) was treated with cyclohexyl amine (44.1 µL, 0.39 mmol) and triethylamine (56.5 µL, 0.39 mmol) to give compound 5 as a white solid (89 mg, 80%).

$^1$H-NMR (CDCl$_3$, ppm): 7.96 (d, 1H), 7.56 (d, 1H), 7.47-7.40 (m, 2H), 7.24-7.09 (m, 3H), 6.74 (d, 1H), 3.97-3.91 (m, 1H), 2.03-1.99 (m, 2H), 1.77-1.62 (m, 4H), 1.47-1.05 (m, 4H).

ES-MS: 468.0 (M+1), 490.0 (M+23).

EXAMPLE 6 Preparation of Compound 6

1-(2,4-dichlorophenyl)-4-methyl-N-(piperidin-1-yl)-5-(selenophen-2-yl)-1H-pyrazole-3-carboxamide Intermediate I(b), lithium salt of ethyl 3-methyl-2,4-dioxo-4-(selenophene-2-yl-butanonte), was prepared in a 36% yield in a manner similar to that used to prepare Intermediate I(a) described in Example 1 except that 1-(selenophene-2-yl) ethanone was replaced with 1-(selenophene-2-yl)propanone.

Intermediate II(b), 1-(2,4-dichloro-phenyl)-4-methyl-5-selenophen-2-yl-1H-pyrazole-3-carboxylic acid ethyl ester, was prepared from Intermediate I(b) in a 50% yield in a manner similar to that used to prepare Intermediate II(a) described in Example 1.

Intermediate III(b), 1-(2,4-dichloro-phenyl)-4-methyl-5-selenophen-2-yl-1H-pyrazole-3-carboxylic acid, was prepared from Intermediate II(b) in a 95% yield in a manner similar to that used to prepare Intermediate III(a) described in Example 1.

Compound 6 was prepared from Intermediate III(b) in a manner similar to that described in Example 1 except that the crude 1-(2,4-dichloro-phenyl)-4-methyl-5-selenophen-2-yl-1H-pyrazole-3-carboxylic chloride (100 mg, 0.24 mmol), instead of 1-(2,4-dichloro-phenyl)-5-selenophen-2-yl-1H-pyrazole-3-carboxylic chloride, was treated with 1-aminopiperidine (41.0 µL, 0.38 mmol) and triethylamine (54.3 µL, 0.38 mmol) to give compound 6 as a white solid (75 mg, 65%).

$^1$H-NMR (CDCl$_3$, ppm): 8.05 (d, 1H), 7.61 (brs, 1H), 7.48 (brs, 1H), 7.33 (brs, 2H), 7.23 (dd, 1H), 7.09 (d, 1H), 2.85-2.84 (m, 4H), 2.47 (s, 3H), 1.76-1.25 (m, 6H);

ES-MS (M+23): 483.0.

EXAMPLE 7 Preparation of Compound 7

N-cycloheptyl-1-(2,4-dichlorophenyl)-4-methyl-5-(selenophen-2-yl)-1H-pyrazole-3-carboxamide Compound 7 was prepared in a manner similar to that described in Example 6 except that, in the last step, the crude carboxylic chloride (100 mg, 0.24 mmol) was treated with cycloheptyl amine (43.4 µL, 0.38 mmol) and triethylamine (54.3 µL, 0.38 mmol) to give compound 7 as a white solid (86 mg, 73%).

$^1$H-NMR (CDCl$_3$, ppm): 8.05 (d, 1H), 7.48 (brs, 1H), 7.34 (brs, 2H), 7.22 (dd, 1H), 7.09 (d, 1H), 6.88 (d, 1H), 4.13-4.11 (m, 1H), 2.48 (s, 3H), 2.06-1.52 (m, 12H);

ES-MS (M+23): 518.

EXAMPLE 8 Preparation of Compound 8

N-cyclohexyl-1-(2,4-dichlorophenyl)-4-methyl-5-(selenophen-2-yl)-1H-pyrazole-3-carboxamide Compound 8 was prepared in a manner similar to that described in Example 6 except that, in the last step, the crude carboxylic chloride (100 mg, 0.24 mmol) was treated with cyclohexyl amine (43.5 µL, 0.38 mmol) and triethylamine (54.3 µL, 0.38 mmol) to give compound 8 as a white solid (97 mg, 84%).

$^1$H-NMR (CDCl$_3$, ppm): 8.04 (d, 1H), 7.47 (brs, 1H), 7.33 (brs, 2H), 7.22 (brs, 1H), 7.09 (brs, 1H), 6.84 (d, 1H), 3.95-3.93 (m, 1H), 2.48 (s, 3H), 2.01-1.15 (m, 10H);

ES-MS (M+23): 503.9.

EXAMPLE 9 Preparation of Compound 9

N-cyclopentyl-1-(2,4-dichlorophenyl)-4-methyl-5-(selenophen-2-yl)-1H-pyrazole-3-carboxamide Compound 9 was prepared in a manner similar to that described in Example 6 except that, in the last step, the crude carboxylic chloride (100 mg, 0.24 mmol) was treated with cyclopentyl amine (37.6 µL, 0.38 mmol) and triethylamine (54.3 µL, 0.38 mmol) to give compound 9 as a white solid (92 mg, 82%).

$^1$H-NMR (CDCl$_3$, ppm): 8.05 (d, 1H), 7.47 (brs, 1H), 7.33 (brs, 2H), 7.22 (d, 1H), 7.09 (d, 1H), 6.87 (d, 1H), 4.38 (dtt, 1H), 2.48 (s, 3H), 2.07-1.47 (m, 8H).

ES-MS (M+23): 490.0.

EXAMPLE 10 Preparation of Compound 10

5-(5-bromoselenophen-2-yl)-N-cyclopentyl-1-(2,4-dichlorophenyl)-4-methyl-1H-pyrazole-3-carboxamide To a magnetically stirred solution of Intermediate II(b) (300 mg, 0.70 mmol) prepared in Example 6 in acetonitrile was added NBS (85 mg, 0.48 mmol) in small portions at 0° C. After the mixture was stirred for 1 hour at 0° C., a saturated sodium sulfite aqueous solution was added. The solvent was evaporated and the resultant residue was extracted with ethyl acetate. The combined extracts were washed sequentially with water, a saturated sodium bicarbonate aqueous solution, and brine. The organic layer was separated, dried over anhydrous sodium sulfate, filtered, and concentrated to give a crude product, which was purified by flash chromatography on silica gel with n-hexane/ethyl acetate (9:1) to give Intermediate II(c), 4-methyl-5-(5-bromo-selenophen-2-yl)-1-(2,4-dichloro-phenyl)-1H-pyrazole-3-carboxylic acid ethyl ester, as a white solid (177 mg, 75%).

A solution of potassium hydroxide (38.0 mg, 0.68 mmol) in methanol (5 mL) was added to a magnetically stirred solution of Intermediate II(c) (177 mg, 0.34 mmol) in methanol (5 mL). The mixture was heated under reflux for 3 hours. The reaction mixture was cooled, poured into water, and acidified with a 10% hydrochloric acid aqueous solution. The precipitate was filtered, washed with water, and dried under vacuum to give Intermediate III(c), i.e., 4-methyl-5-(5-bromo-selenophen-2-yl)-1-(2,4-dichlorophenyl)-1H-pyrazole-3-carboxylic acid, as a white solid (155 mg, 95%).

A solution of Intermediate III(c) (100 mg, 0.20 mmol) and thionyl chloride (51.0 µL, 0.70 mmol) in toluene (5 mL) was refluxed for 3 hours. The solvent was evaporated under reduced pressure. The resultant residue was re-dissolved in toluene (5 mL) and concentrated again to yield a crude carboxylic chloride (99 mg, 96%) as a light solid. The carboxylic chloride dissolved in dichloromethane (5 mL) was added dropwise to a mixture of cyclopentyl amine (31.7 µL, 0.32 mmol) and triethylamine (44.6 µL, 0.32 mmol) in 5 mL of dichloromethane at 0° C. After the mixture was stirred at room temperature for 3 hours, the reaction was quenched with water. The aqueous layer was separated and extracted with dichloromethane (2×10 mL). The combined extracts were washed with brine, dried over anhydrous sodium sulfate, filtered, and concentrated to give a crude product, which was purified by flash column chromatography on silica gel with n-hexane/ethyl acetate (2:1) to give compound 10 as a white solid (87 mg, 80%).

$^1$H-NMR (CDCl$_3$, ppm): 7.50 (d, 1H), 7.38 (d, 1H), 7.38 (s, 1H), 7.16 (d, 1H), 6.87 (d, 1H), 6.82 (d, 1H), 4.36 (dtt, 1H), 2.46 (s, 3H), 2.09-2.02 (m, 2H), 1.73-1.46 (m, 8H).

ES-MS (M+23): 567.8.

EXAMPLE 11 Preparation of Compound 11

5-(5-bromoselenophen-2-yl)-1-(2,4-dichlorophenyl)-N-(hexahydrocyclopenta[c]pyrrol-2(1H)-yl)-4-methyl-1H-pyrazole-3-carboxamide Compound 11 was prepared in a manner similar to that described in Example 10 except that, in the last step, the crude carboxylic chloride (100 mg, 0.20 mmol) was treated with hexahydrocyclopenta-[c]pyrrol-2(1H)-amine hydrochloride (52 mg, 0.32 mmol) and triethylamine (72.5 µL, 0.52 mmol) to give Compound 11 as a white solid (81 mg, 70%).

$^1$H-NMR (CDCl$_3$, ppm): 7.50 (d, 1H), 7.47 (brs, 1H), 7.35 (d, 1H), 7.33 (brs, 1H), 7.15 (d, 1H), 6.81 (d, 1H), 3.25 (t, 2H), 2.66 (brs, 2H), 2.49 (d, 2H), 2.45 (s, 3H), 1.66-1.49 (m, 6H).

ES-MS (M+1): 586.8.

EXAMPLE 12 Preparation of Compound 12

5-(5-bromoselenophen-2-yl)-N-cyclohexyl-1-(2,4-dichlorophenyl)-4-methyl-1H-pyrazole-3-carboxamide Compound 12 was prepared in a manner similar to that described in Example 10 except that, in the last step, the crude carboxylic chloride (100 mg, 0.20 mmol) was treated with cyclohexyl amine (36.5 µL, 0.32 mmol) and triethylamine (44.6 µL, 0.32 mmol) to give compound 12 as a white solid (84 mg, 75%).

$^1$H-NMR (CDCl$_3$, ppm): 7.50 (d, 1H), 7.38 (d, 1H), 7.35 (d, 1H), 7.35 (s, 1H), 7.15 (d, 1H), 6.81 (d, 1H), 6.79 (brs, 1H), 3.95-3.88 (m, 1H), 2.42 (s, 3H), 1.99-1.59 (m, 6H), 1.45-1.32 (m, 4H).

ES-MS (M+23): 581.8.

EXAMPLE 13 Preparation of Compound 13

5-(5-bromoselenophen-2-yl)-1-(2,4-dichlorophenyl)-4-methyl-N-(piperidin-1-yl)-1H-pyrazole-3-carboxamide Compound 13 was prepared in a manner similar to that described in Example 10 except that, in the last step, the crude carboxylic chloride (100 mg, 0.20 mmol) was treated with 1-aminopiperidine (34.5 µL, 0.32 mmol) and triethylamine (44.6 µL, 0.32 mmol) to give compound 13 as a white solid (78 mg, 70%).

$^1$H-NMR (CDCl$_3$, ppm): 7.59 (brs, 1H), 7.51 (d, 1H), 7.36 (d, 1H), 7.34 (s, 1H), 7.6 (d, 1H), 6.81 (d, 1H), 2.84 (brs, 2H), 2.45 (s, 3H), 1.77-1.24 (m, 8H)

ES-MS (M+1): 562.8.

EXAMPLE 14 Preparation of Compound 14

4-bromo-5-(5-bromoselenophen-2-yl)-N-cyclopentyl-1-(2,4-dichlorophenyl)-1H-pyrazole-3-carboxamide To a magnetically stirred solution of Intermediate II(a) (500 mg, 1.20 mmol) in acetonitrile was added NBS (640 mg, 3.6 mmol) in a small portions at 0° C. The resultant mixture was stirred at room temperature for 48 hours. The precipitate was filtered, washed with a saturated sodium sulfite aqueous solution and cold water, and then dried over vacuum to give Intermediate II(d), i.e., 4-bromo-5-(5-bromo-selenophen-2-yl)-1-(2,4-dichloro-phenyl)-1H-pyrazole-3-carboxylic acid ethyl ester, as a white solid (630 mg, 92%).

A solution of potassium hydroxide (117 mg, 2.10 mmol) in methanol (5 mL) was added to a magnetically stirred solution of Intermediate II(d) (600 mg, 1.05 mmol) in methanol (5 mL). The mixture was heated under reflux for 3 hours. The reaction mixture was cooled, poured into water, and acidified with a 10% hydrochloric acid aqueous solution. The precipitate was filtered, washed with water, and dried under vacuum to give Intermediate III(d), i.e., 4-bromo-5-(5-bromo-selenophen-2-yl)-1-(2,4-dichlorophenyl)-1H-pyrazole-3-carboxylic acid, as a white solid (542 mg, 95%).

A solution of Intermediate III(d) (100 mg, 0.18 mmol) and thionyl chloride (46.1 µL, 0.63 mmol) in toluene (5 mL) was refluxed for 3 hours. The solvent was then evaporated under reduced pressure. The resultant residue was re-dissolved in toluene (5 mL) and concentrated again to yield a crude 1-(2,4-dichloro-phenyl)-4-bromo-5-(5-bromo-selenophen-2-yl)-1H-pyrazole-3-carboxylic chloride (98 mg, 95%) as a light solid. The carboxylic chloride dissolved in dichloromethane (5 mL) was added dropwise to a mixture of cyclopentyl amine (26.7 µL, 0.27 mmol) and triethylamine (38.6 µL, 0.27 mmol) in 5 mL of dichloromethane at 0° C. After the mixture was stirred at room temperature for 3 hours, the reaction was quenched with water. The aqueous layer was separated and extracted with dichloromethane (2×10 mL). The combined extracts were washed with brine, dried over anhydrous sodium sulfate, filtered, and concentrated to give a crude product, which was purified by flash column chromatography on silica gel with n-hexane/ethyl acetate (2:1) to give compound 14 as a white solid (86 mg, 83%).

$^1$H-NMR (CDCl$_3$, ppm): 7.53 (d, 1H), 7.40 (d, 1H), 7.38 (s, 1H), 7.15 (d, 1H), 6.98 (d, 1H), 6.77 (d, 1H), 4.38 (dtt, 1H), 2.10-2.02 (m, 2H), 1.72-1.48 (m, 6H).

ES-MS (M+23): 631.8.

EXAMPLE 15 Preparation of Compound 15

4-bromo-5-(5-bromoselenophen-2-yl)-1-(2,4-dichlorophenyl)-N-(piperidin-1-yl)-1H-pyrazole-3-carboxamide Compound 15 was prepared in a manner similar to that described in Example 14 except that, in the last step, the crude carboxylic chloride (100 mg, 0.17 mmol) was treated with 1-aminopiperidine (29.1 µL, 0.27 mmol) and triethylamine (38.6 µL, 0.27 mmol) to give compound 15 as a white solid (74 mg, 70%).
¹H-NMR (CDCl₃, ppm): 7.54 (d, 2H), 7.43-7.36 (m, 2H), 7.15 (d, 1H), 6.98 (d, 1H), 2.87 (t, 4H), 1.77-1.42 (m, 6H).
ES-MS (M+1): 624.8.

EXAMPLE 16 Preparation of Compound 16

4-bromo-5-(5-bromoselenophen-2-yl)-N-cyclohexyl-1-(2,4-dichlorophenyl)-1H-pyrazole-3-carboxamide Compound 16 was prepared in a manner similar to that described in Example 14 except that, in the last step, the crude carboxylic chloride (100 mg, 0.17 mmol) was treated with cyclohexyl amine (30.9 µL, 0.27 mmol) and triethylamine (38.6 µL, 0.27 mmol) to give compound 16 as a white solid (85 mg, 80%).
¹H-NMR (CDCl₃, ppm): 7.53 (d, 1H), 7.43 (d, 1H), 7.42 (s, 1H), 7.15 (d, 1H), 6.98 (d, 1H), 6.70 (d, 1H), 3.97-3.94 (m, 1H), 2.04-1.98 (m, 2H), 1.76-1.15 (m, 8H).
ES-MS (M+1): 623.7.

EXAMPLE 17 Preparation of Compound 17

4-bromo-5-(5-bromoselenophen-2-yl)-1-(2,4-dichlorophenyl)-N-(1,2,3,4-tetrahydronaphthalen-1-yl)-1H-pyrazole-3-carboxamide Compound 17 was prepared in a manner similar to that described in Example 14 except that, in the last step, the crude carboxylic chloride (100 mg, 0.17 mmol) was treated with 1,2,3,4-tetrahrdro-1-naphthyl amine (38.9 zL, 0.27 mmol) and triethylamine (38.6 µL, 0.27 mmol) to give compound 17 as a white solid (74 mg, 65%).
¹H-NMR (CDCl₃, ppm): 7.50 (d, 1H), 7.37 (d, 1H), 7.35 (s, 1H), 7.26 (brs, 2H), 7.18-7.08 (m, 3H), 6.98 (d, 1H), 5.39 (dt, 1H), 2.82-2.77 (m, 2H), 2.17-1.87 (m, 4H).
ES-MS (M+23): 693.6.

EXAMPLE 18 Preparation of Compound 18

(4-bromo-5-(5-bromoselenophen-2-yl)-1-(2,4-dichlorophenyl)-1H-pyrazol-3-yl)(3,4-dihydroisoquinolin-2(1H)-yl)methanone Compound 18 was prepared in a manner similar to that described in Example 14 except that, in the last step, the crude carboxylic chloride (100 mg, 0.17 mmol) was treated with 1,2,3,4-tetrahrdroisoquinoline (38.6 µL, 0.27 mmol) and triethylamine (38.6 µL, 0.27 mmol) to give compound 18 as a white solid (61 mg, 55%).
¹H-NMR (CDCl₃, ppm): 7.55 (d, 1H), 7.38 (d, 1H), 7.35 (s, 1H), 7.22-7.16 (m, 5H), 7.03 (d, 1H), 4.95 (brs, 2H), 3.85 (t, 2H), 2.30-2.94 (m, 2H).
ES-MS (M+23): 679.7.

EXAMPLE 19 Preparation of Compound 19

4-bromo-5-(5-bromoselenophen-2-yl)-1-(2,4-dichlorophenyl)-N-(hexahydrocyclopenta[c]pyrrol-2(1H)-yl)-1H-pyrazole-3-carboxamide Compound 19 was prepared in a manner similar to that described in Example 14 except that, in the last step, the crude carboxylic chloride (100 mg, 0.17 mmol) was treated with hexahydrocyclopenta-[c]pyrrol-2(1H)-amine hydrochloride (44.0 mg, 0.27 mmol) and triethylamine (62.9 µL, 0.44 mmol) to give compound 19 as a white solid (88 mg, 80%).
¹H-NMR (CDCl₃, ppm): 7.54 (d, 1H), 7.39 (d, 1H), 7.37 (s, 1H), 7.15 (d, 1H), 6.98 (d, 1H), 3.27 (t, 2H), 2.65 (brs, 2H), 2.54 (d, 1H), 2.52 (d, 1H), 1.67-1.50 (m, 6H).
ES-MS (M+1): 650.7.

EXAMPLE 20 Preparation of Compound 20

4-bromo-5-(5-bromoselenophen-2-yl)-1-(2,4-dichlorophenyl)-N-hexyl-1H-pyrazole-3-carboxamide Compound 20 was prepared in a manner similar to that described in Example 14 except that, in the last step, the crude carboxylic chloride (100 mg, 0.17 mmol) was treated with hexylamine (35.9 µL, 0.27 mmol) and triethylamine (38.6 µL, 0.27 mmol) to give compound 20 as a white solid (88 mg, 80%).
¹H-NMR (CDCl₃, ppm): 7.54 (d, 1H), 7.40 (d, 1H), 7.38 (s, 1H), 7.16 (d, 1H), 6.98 (d, 1H), 6.85 (t, 1H) 3.41 (q, 2H), 1.63-1.25 (m, 8H) 0.87 (t, 3H).
ES-MS (M+1): 625.9.

EXAMPLE 21 Preparation of Compound 21

4-bromo-5-(5-bromoselenophen-2-yl)-N-(2-cyclohexenylethyl)-1-(2,4-dichlorophenyl)-1H-pyrazole-3-carboxamide Compound 21 was prepared in a manner similar to that described in Example 14 except that, in the last step, the crude carboxylic chloride (50 mg, 0.07 mmol) was treated with 2-cyclohexenylethanamine (15.3 µL, 0.11 mmol) and triethylamine (15.7 µL, 0.11 mmol) to give compound 21 as a white solid (50 mg, 85%).
¹H-NMR (CDCl₃, ppm): 7.53 (d, 1H), 7.42 (d, 1H), 7.39 (s, 1H), 7.16 (d, 1H), 6.98 (d, 1H), 6.86 (brs, 1H), 5.49 (brs, 1H), 3.51 (q, 2H), 2.22 (t, 2H), 1.97-1.53 (m, 8H).
ES-MS (M+1): 649.8.

EXAMPLE 22 Preparation of Compound 22

4-bromo-5-(5-bromoselenophen-2-yl)-N-cycloheptyl-1-(2,4-dichlorophenyl)-1H-pyrazole-3-carboxamide Compound 22 was prepared in a manner similar to that described in Example 14 except that, in the last step, the crude carboxylic chloride (50 mg, 0.07 mmol) was treated with cycloheptyl amine (12.4 µL, 0.11 mmol) and triethylamine (15.7 µL, 0.11 mmol) to give compound 22 as a white solid (48 mg, 82%).
¹H-NMR (CDCl₃, ppm): 7.50 (d, 1H), 7.47 (brs, 1H), 7.35 (d, 1H), 7.33 (brs, 1H), 7.15 (d, 1H), 6.81 (d, 1H), 3.25 (t, 2H), 2.66 (brs, 2H), 2.49 (d, 2H), 2.45 (s, 3H), 1.66-1.49 (m, 6H).
ES-MS (M+1): 637.8.

EXAMPLE 23 Preparation of Compound 23

4-bromo-5-(5-bromoselenophen-2-yl)-N-(2-admantyl)-1-(2,4-dichlorophenyl)-1H-pyrazole-3-carboxamide Compound 23 was prepared in a manner similar to that described in Example 14 except that, in the last step, the crude carboxylic chloride (50 mg, 0.07 mmol) was treated with 1-admantylethyl amine (226 µL, 0.11 mmol), and triethylamine (15.7 µL, 0.11 mmol) gave compound 23 as a white solid (48 mg, 75%).
¹H-NMR (CDCl₃, ppm): 7.53 (brs, 1H), 7.41 (brs, 1H), 7.40 (s, 1H), 7.15 (d, 1H), 6.98 (d, 1H), 6.74 (d, 1H), 3.90 (dq, 1H), 1.98 (brs, 3H), 1.75-1.52 (m, 10H), 1.11 (d, 3H).

EXAMPLE 24 Preparation of Compound 24

4-bromo-5-(5-bromoselenophen-2-yl)-1-(2,4-dichlorophenyl)-N-(((1R,2R,5R)-6,6-dimethylbicyclo[3.1.1]heptan-2-yl)methyl)-1H-pyrazole-3-carboxamide Compound 24 was prepared in a manner similar to that described in Example 14 except that, in the last step, the crude carboxylic chloride (50 mg, 0.07 mmol) was treated with ((1R,2R,5R)-6,6-dimethylbicyclo[3.1.1]heptan-2-yl)methanamine (16.1 µL, 0.11 mmol) and triethylamine (15.7 µL, 0.11 mmol) to give compound 24 as a white solid (45 mg, 73%).
¹H-NMR (CDCl₃, ppm): 7.51 (d, 1H), 7.37 (d, 1H), 7.33 (s, 1H), 7.12 (d, 1H), 6.95 (d, 1H), 6.84 (brs, 1H), 3.50-3.29 (m, 2H), 2.35-2.22 (m, 2H), 1.93-1.80 (m, 7H), 1.16 (s, 3H), 1.03 (s, 3H).
ES-MS (M+1): 677.8.

EXAMPLE 25 Preparation of Compound 25

(4-bromo-5-(5-bromoselenophen-2-yl)-1-(2,4-dichlorophenyl)-1H-pyrazol-3-yl)(octahydroisoquinolin-2(1H)-yl)methanone Compound 25 was prepared in a manner similar to that described in Example 14 except that, in the last step, the crude carboxylic chloride (50 mg, 0.07 mmol) was treated with decahydroisoquinoline (15.3 µL, 0.11 mmol) and triethylamine (15.7 µL, 0.11 mmol) to give compound 25 as a white solid (39 mg, 65%).
¹H-NMR (CDCl₃, ppm): 7.50 (d, 1H), 7.33-7.31 (m, 2H), 7.13 (d, 1H), 6.98 (d, 1H), 4.79 (d, 1H), 4.62 (d, 1H), 3.92 (d, 1H), 3.76 (d, 1H), 3.08 (dt, 1H), 2.76-2.65 (m, 2H), 2.35 (t, 1H), 1.70-0.95 (m, 8H)
ES-MS (M+1): 663.8.

EXAMPLE 26 Preparation of Compound 26

(4-bromo-5-(5-bromoselenophen-2-yl)-1-(2,4-dichlorophenyl)-1H-pyrazol-3-yl)(octahydroisoquinolin-2(1H)-yl)methanone Compound 26 was prepared in a manner similar to that described in Example 14 except that, in the last step, the crude carboxylic chloride (100 mg, 0.17 mmol) was treated with n-nonylamine (49.5 µL, 0.27 mmol) and triethylamine (38.6 µL, 0.27 mmol) to give compound 26 as a white solid (88 mg, 80%).
¹H-NMR (CDCl₃, ppm): 7.53 (d, 1H), 7.40 (d, 1H), 7.39 (s, 1H), 7.15 (d, 1H), 6.98 (d, 1H), 6.86 (t, 1H) 3.41 (q, 2H), 1.60-1.25 (m, 8H) 0.86 (t, 3H).
ES-MS (M+1): 667.9.

EXAMPLE 27 Preparation of Compound 27

5-(5-bromoselenophen-2-yl)-N-cyclopentyl-1-(2,4-dichlorophenyl)-1H-pyrazole-3-carboxamide To a magnetically stirred solution of Intermedate II(a) (200 mg, 0.48 mmol) prepared in Example 1 in acetonitrile was added NBS (85 mg, 0.48 mmol) in small portions at 0° C. After the mixture was stirred for 1 hour at 0° C., a saturated sodium sulfite aqueous solution was added. The solvent was evaporated and the resultant residue was extracted with ethyl acetate. The combined extracts were washed sequentially with water, a saturated sodium bicarbonate aqueous solution, and brine. The organic layer was separated, dried over anhydrous sodium sulfate, filtered, and concentrated to give a crude product, which was purified by flash chromatography on silica gel with n-hexane/ethyl acetate (9:1) to give Intermediate II(e). i.e., 5-(5-bromo-selenophen-2-yl)-1-(2,4-dichloro-phenyl)-1H-pyrazole-3-carboxylic acid ethyl ester, as a white solid (177 mg, 75%).

A solution of potassium hydroxide (19 mg, 0.68 mmol) in methanol (5 mL) was added to a magnetically stirred solution of Intermediate II(e) (170 mg, 0.34 mmol) in methanol (5 mL). The mixture was heated under reflux for 3 hours. The reaction mixture was cooled, poured into water, and acidified with a 10% hydrochloric acid aqueous solution. The precipitate was filtered, washed with water, and dried under vacuum to give Intermediate III(e), i.e., 5-(5-bromo-selenophen-2-yl)-1-(2,4-dichlorophenyl)-1H-pyrazole-3-carboxylic acid, as a white solid (147 mg, 92%).

A solution of Intermediate III(e) (100 mg, 0.21 mmol) and thionyl chloride (67.1 µL, 0.92 mmol) in toluene (5 mL) was refluxed for 3 hours. The solvent was evaporated under reduced pressure. The resultant residue was re-dissolved in toluene (5 mL) and concentrated again to give the crude carboxylic chloride as a light solid (98 mg, 95%). The carboxylic chloride dissolved in dichloromethane (5 mL) was added dropwise to a mixture of cyclopentyl amine (31.7 µL, 0.32 mmol) and triethylamine (44.6 µL, 0.32 mmol) in 5 mL of dichloromethane at 0° C. After the mixture was stirred at room temperature for 3 hours, the reaction was quenched with water. The aqueous layer was separated and extracted with dichloromethane (2×10 mL). The combined extracts were washed with brine, dried over anhydrous sodium sulfate, filtered, and concentrated to give a crude product, which was purified by flash column chromatography on silica gel with n-hexane/ethyl acetate (2:1) to give compound 27 as a white solid (85 mg, 80%).
¹H-NMR (CDCl₃, ppm): 7.58 (d, 1H), 7.44 (brs, 2H), 7.13 (d, 1H), 7.08 (s, 1H), 6.90 (d, 1H), 4.42-4.35 (m, 1H), 2.09-2.01 (m, 2H), 1.71-1.46 (m, 6H).
ES-MS (M+1): 531.8.

EXAMPLE 28 Preparation of Compound 28

N-cyclohexyl-1-(2,4-dichlorophenyl)-4-methyl-5-(5-methylselenophen-2-yl)-1H-pyrazole-3-carboxamide A solution of compound 16 (50 mg, 0.08 mmol), methyl zinc chloride (24.0 µL, 0.24 mmol), tetrakis-triphenylphosphinopallidum (5 mg, 0.004 mmol), and THF (5 mL) was refluxed for 24 hours. The solvent was then evaporated under reduced pressure. The resultant residue was purified by flash column chromatography with n-hexane/ethyl acetate (5:1) to give compound 28 as a white solid (23 mg, 60%).
¹H-NMR (CDCl₃, ppm): 7.49 (d, 1H), 7.34 (brs, 1H), 7.38 (brs, 1H), 6.87 (d, 1H), 6.81 (brs, 1H), 6.80 (d, 1H), 2.50 (s, 3H), 2.48 (s, 3H), 2.00-1.98 (m, 2H), 1.77-1.50 (m, 8H).
ES-MS (M+1): 496.0.

EXAMPLE 29 Preparation of Compound 29

(E)-4-bromo-5-(5-(pent-1-enyl)selenophen-2-yl)-1-(2,4-dichlorophenyl)-N-(hexahydrocyclopenta[c]pyrrol-2(1H)-yl)-1H-pyrazole-3-carboxamide A solution of Intermediate II(d) (100 mg, 0.17 mmol) prepared in Example 14, pent-1-enylboronic acid (23.2 mg, 0.20 mmol), tetrakis-triphenylphosphinopallidum (10 mg, 0.008 mmol), and cesium carbonate (110 mg, 0.34 mmol) in DME (5 mL) was refluxed for 3 hours. The solvent was then evaporated under reduced pressure. The resultant residue was purified by flash column chromatography with n-hexane/ethyl acetate (5:1) to give Intermediate IV, i.e., 4-bromo-1-(2,4-dichlorophenyl)-5-[((E)-5-pent-1-enyl)-selenophen-2-yl]-1H-pyrazole-3-carboxylic acid ethyl ester, as a light solid (65 mg, 70%).

Compound 29 was prepared from Intermediate IV in a manner similar to that described in the last step of Example 14 except that the crude carboxylic chloride (50 mg, 0.09 mmol) was treated with hexahydrocyclopenta-[c]pyrrol-2(1H)-amine hydrochloride (23 mg, 0.14 mmol), and triethylamine (32.2 µL, 0.22 mmol) to give compound 29 as a white solid (40 mg, 72%).

1H-NMR (CDCl$_3$, ppm): 7.49 (d, 1H), 7.38-7.36 (m, 2H), 7.08 (d, 1H), 6.84 (d, 1H), 6.42 (d, 1H), 5.93 (dt, 1H), 3.31-3.26 (m, 2H), 2.65-2.56 (m, 4H), 2.13-1.21 (m, 10H), 0.90 (t, 3H).

EXAMPLE 30 Preparation of Compound 30

[4-bromo-5-[5-((E)-2-cyclohexylvinyl)-selenophen-2-yl]-1-(2,4-dichlorophenyl)-1H-pyrazol-3-yl]-piperidin-1-yl-methanone Compound 30 was prepared in a manner similar to that described in Example 29 except that but-1-enylboronic acid was replaced with (E)-2-cyclohexylvinylboronic.

$^1$H-NMR (CDCl$_3$, ppm): 7.52 (s, 1H), 7.39-7.38 (m, 2H), 7.11 (d, 1H), 6.87 (d, 1H), 6.40 (d, 1H), 5.91 (dd, 1H), 3.75 (brs, 2H), 3.51 (brs, 2H), 1.77-1.07 (m, 6H).

EXAMPLE 31 Preparation of Compound 31

5-[5-(4-chlorophenyl)-selenophen-2-yl]-1-(2,4-dichlorophenyl)-4-methyl-1H-pyrazole-3-carboxylic acid cyclohexylamide Compound 31 was prepared in a manner similar to that described in Example 29 except that but-1-enylboronic acid was replaced with 4-chlorophenylboronic acid.

$^1$H-NMR (CDCl$_3$, ppm): 7.50 (d, 1H), 7.39-7.28 (m, 7H), 6.82 (d, 1H), 3.98-3.91 (m, 1H), 2.53 (s, 3H), 2.02-1.15 (m, 10H).

EXAMPLE 32 Preparation of Compound 32

4-bromo-5-[5-((E)-2-cyclohexylvinyl)-selenophen-2-yl]-1-(2,4-dichlorophenyl)-1H-pyrazole-3-carboxylic acid piperidin-1-ylamide Compound 32 was prepared in a manner similar to that described in Example 29 except that but-1-enylboronic acid was replaced with (E)-2-cyclohexylvinylboronic.

$^1$H-NMR (CDCl$_3$, ppm): 7.55 (s, 1H), 7.52 (s, 1H), 7.40-7.39 (m, 2H), 7.08 (d, 1H), 6.87 (d, 1H), 6.40 (d, 1H), 5.91 (dd, 1H), 2.88 (t, 4H), 2.07-0.85 (m, 17H).

EXAMPLE 33 Preparation of Compound 33

4-bromo-5-[5-((E)-2-cyclohexylvinyl)-selenophen-2-yl]-1-(2,4-dichlorophenyl)-1H-pyrazole-3-carboxylic acid hexylamide Compound 33 was prepared in a manner similar to that described in Example 29 except that but-1-enylboronic acid was replaced with (E)-2-cyclohexylvinylboronic acid.

$^1$H-NMR (CDCl$_3$, ppm): 7.52 (d, 1H), 7.40-7.39 (m, 2H), 7.09 (d, 1H), 6.87 (d, 1H), 6.40 (d, 1H), 5.91 (dd, 1H), 3.41 (q, 2H), 2.07-1.39 (m, 19H), 0.88 (t, 3H).

EXAMPLE 34 Preparation of Compound 34

1-(4-bromo-5-(5-bromoselenophen-2-yl)-1-(2,4-dichlorophenyl)-1H-pyrazol-3-yl)-3-(pyrrolidin-1-yl)propane-1,3-dione To a magnetically stirred solution of lithium bis(trimethylsilyl)amide (22.2 µL, 0.20 mmol) in THF (5 mL) was added a solution of 1-pyrrolidin-1-yl-ethanone (21 mg, 0.18 mmol) in THF (3 mL) at −78° C. After the mixture was stirred at the same temperature for additional 45 minutes, the crude 1-(2,4-dichloro-phenyl)-4-bromo-5-(5-bromo-selenophen-2-yl-1H-pyrazole-3-carboxylic chloride (100 mg, 0.17 mmol) prepared in the last step of Example 14 was added. After the mixture was stirred at the same temperature for another 30 minutes, the reaction was quenched with water. The aqueous layer was separated and extracted with ethyl acetate (2×10 mL). The combined extracts were washed with brine, dried over anhydrous sodium sulfate, filtered, and concentrated to give a crude product, which was purified by flash column chromatography on silica gel with n-hexane/ethyl acetate (5:1) to give compound 34 as a white solid (76 mg, 70%).

$^1$H-NMR (CDCl$_3$, ppm): 7.54 (d, 1H), 7.50 (d, 1H), 7.42-7.39 (m, 2H), 7.16 (d, 1H), 6.98 (d, 1H), 6.05 (s, 1H), 4.09 (s, 2H), 3.58-3.46 (m, 4H), 1.99-1.25 (m, 4H).

ES-MS (M+1): 737.8.

EXAMPLE 35 Preparation of Compound 35

3-(4-bromo-5-(5-bromoselenophen-2-yl)-1-(2,4-dichlorophenyl)-1H-pyrazol-3-yl)-N,N-diethyl-3-oxopropanamide Compound 35 was prepared in a manner similar to that described in Example 34 except that the crude carboxylic chloride (100 mg, 0.17 mmol) was treated with lithium bis(trimethylsilyl)amide (22.2 µL, 0.20 mmol) and N,N-diethylacetamide (21 mg, 0.18 mmol) to give compound 35 as a white solid (81 mg, 75%).

$^1$H-NMR (CDCl$_3$, ppm): 7.54 (d, 1H), 7.50 (d, 1H), 7.40-7.39 (m, 2H), 7.16 (d, 1H), 6.97 (d, 1H), 6.15 (s, 1H), 4.11 (s, 2H), 3.45-3.30 (m, 4H), 1.25-1.11 (m, 6H).

ES-MS (M+1): 639.8.

EXAMPLE 36 Preparation of Compound 36

1-(4-bromo-5-(5-bromoselenophen-2-yl)-1-(2,4-dichlorophenyl)-1H-pyrazol-3-yl)-3-(piperidin-1-yl)propane-1,3-dione Compound 36 was prepared in a manner similar to that described in Example 34 except that the crude carboxylic chloride (100 mg, 0.17 mmol) was treated with lithium bis (trimethylsilyl)amide (22.2 µL, 0.20 mmol) and 1-piperidin-1-yl-ethanone (23 mg, 0.18 mmol) to give compound 36 as a white solid (86 mg, 78%).

$^1$H-NMR (CDCl$_3$, ppm): 7.54 (d, 1H), 7.50 (d, 1H), 7.42-7.38 (m, 2H), 7.16 (d, 1H), 6.98 (d, 1H), 6.20 (s, 1H), 4.16 (s, 2H), 3.60-3.36 (m, 4H), 1.64-1.23 (m, 6H).

ES-MS (M+1): 651.8.

EXAMPLE 37 Preparation of Compound 37

1-(4-bromo-5-(5-bromoselenophen-2-yl)-1-(2,4-dichlorophenyl)-1H-pyrazol-3-yl)-3-(3-methylpiperidin-1-yl)propane-1,3-dione Compound 37 was prepared in a manner similar to that described in Example 34 except that the crude carboxylic chloride (100 mg, 0.17 mmol) was treated with lithium bis(trimethylsilyl)amide (22.2 µL, 0.20 mmol) and 1-(3-methylpiperidin-1-yl)-ethanone (26 mg, 0.18 mmol) to give compound 37 as a white solid (81 mg, 72%).

$^1$H-NMR (CDCl$_3$, ppm): 7.48 (brs, 1H), 7.34 (brs, 2H), 7.10 (d, 1H), 6.91 (d, 1H), 6.14 (s, 1H), 4.37-4.33 (m, 1H), 4.10 (s, 1H), 3.60-3.50 (m, 1H), 2.95-2.21 (m, 2H), 1.76-0.79 (m, 8H).

EXAMPLE 38 Preparation of Compound 38

3-(4-bromo-5-(5-bromoselenophen-2-yl)-1-(2,4-dichlorophenyl)-1H-pyrazol-3-yl)-N,N-diisobutyl-3-oxopropanamide Compound 38 was prepared in a manner similar to that described in Example 34 except that the crude carboxylic chloride (100 mg, 0.17 mmol) was treated with lithium bis(trimethylsilyl)amide (22.2 µL, 0.20 mmol) and N,N-diisobutyl-acetamide (32 mg, 0.18 mmol) to give compound 38 as a white solid (94 mg, 80%).

$^1$H-NMR (CDCl$_3$, ppm): 7.44 (brs, 1H), 7.31 (brs, 2H), 7.09 (d, 1H), 6.90 (d, 1H), 6.15 (brs, 1H), 4.05 (brs, 2H), 3.18-2.93 (m, 4H), 1.95-0.70 (m, 14H).

ES-MS (M+1): 695.8.

EXAMPLE 39 Preparation of Compound 39

1-((4-bromo-5-(5-bromoselenophen-2-yl)-1-(2,4-dichlorophenyl)-1H-pyrazol-3-yl)methyl)-3-cyclohexylurea Lithium aluminum hydride (164 mg, 1.74 mmol) was added to a magnetically stirred solution of Intermediate II(d) (500 mg, 0.87 mmol) in THF (10 mL) at 0° C. After the mixture was stirred at the same temperature for 30 minutes, the reaction was quenched with water. The aqueous layer was separated and extracted with ethyl acetate (2×10 mL). The combined extracts were washed with brine, dried over anhydrous sodium sulfate, filtered, concentrated, and dried under vacuum to give Intermediate V, (4-bromo-5-(5-bromoselenophen-2-yl)-1-(2,4-dichlorophenyl)-1H-pyrazol-3-yl)methanol, as a white solid (438 mg, 95%).

To a magnetically stirred solution of Intermediate V (430 mg, 0.81 mmol) in THF (10 mL) was added triethylamine (127 µL, 0.89 mmol) at 0° C. After the mixture was stirred at the same temperature for 30 minutes, methanesulfonyl chloride (111 µL, 0.97 mmol) was added to the mixture. The mixture was stirred at room temperature for 8 hours. After the reaction was quenched with water, the aqueous layer was separated and extracted with ethyl acetate (2×10 mL). The combined extracts were washed with brine, dried over anhydrous sodium sulfate, filtered, and concentrated to give a crude product, which was purified by flash column chromatography on silica gel with n-hexane/ethyl acetate (4:1) to give Intermediate VI, methanesulfonic acid 4-bromo-5-(5-bromo-selenophen-2-yl)-1-(2,4-dichloro-phenyl)-1H-pyrazol-3-ylmethyl ester, as a white solid (453 mg, 92%).

$^1$H-NMR (CDCl$_3$, ppm): 7.50 (d, 1H), 7.37 (d, 1H), 7.35 (s, 1H), 7.14 (d, 1H), 7.00 (d, 1H), 5.31 (s, 2H), 3.06 (s, 3H).

Sodium azide (96 mg, 1.48 mmol) was added to a magnetically stirred solution of Intermediate VI (450 mg, 0.74 mmol) in DMF (10 mL). The reaction mixture was heated under 80° C. for 3 hours. After the mixture was cooled, the reaction was quenched with water. The aqueous layer was separated and extracted with ethyl acetate (2×10 mL). The combined extracts were washed with brine, dried over anhydrous sodium sulfate, filtered, and concentrated to give a crude product, which was purified by flash column chromatography on silica gel with n-hexane/ethyl acetate (3:1) to give Intermediate VII, 3-azidomethyl-4-bromo-5-(5-bromo-selenophen-2-yl)-1-(2,4-dichloro-phenyl)-1H-pyrazole, as a white solid (308 mg, 75%). $^1$H-NMR (CDCl$_3$, ppm): 7.50 (d, 1H), 7.37 (d, 1H), 7.36 (s, 1H), 7.14 (d, 1H), 7.00 (d, 1H), 4.42 (s, 2H).

Triphenylphosphine (170 mg, 0.64 mmol) was added to a magnetically stirred solution of Intermediate VII (300 mg, 0.54 mmol) in THF and water (10:1). After the mixture was stirred at room temperature for 48 hours, the reaction was extracted with ethyl acetate (2×10 mL). The combined extracts were washed with brine, dried over anhydrous sodium sulfate, filtered, and concentrated to give a crude product, which was purified by flash column chromatography on silica gel with ethyl acetate/methanol (4:1) to give Intermediate VIII, [4-Bromo-5-(5-bromo-selenophen-2-yl)-1-(2,4-dichloro-phenyl)-1H-pyrazol-3-yl]-methylamine, as a white solid (205 mg, 72%).

Isocyanatocyclohexane (14 µL, 0.10 mmol) was added to a magnetically stirred solution of Intermediate VIII (50 mg, 0.09 mmol) in THF. After the mixture was stirred at room temperature for 8 hours, the solvent was evaporated to give a crude product, which was purified by flash column chromatography on silica gel with n-hexane/ethyl acetate (1:1) to give compound 39 as a white solid (41 mg, 70%).

$^1$H-NMR (CDCl$_3$, ppm): 7.50 (d, 1H), 7.35 (d, 1H), 7.33 (s, 1H), 7.13 (d, 1H), 6.96 (d, 1H), 4.42 (s, 2H), 1.87-0.86 (m, 10H).

ES-MS (M+1): 652.8.

EXAMPLE 40 Preparation of Compound 40

1-[1-(2,4-dichlorophenyl)-4-methyl-5-selenophen-2-yl-1H-pyrazol-3-ylmethyl]-3-phenyl-urea Compound 40 was prepared in a manner similar to that described in Example 39 except that Intermediate II(d) in the initial step and isocyanatocyclohexane in the last step were replaced with Intermediate II(b) and isocyanatobenzene, respectively.

$^1$H-NMR (CDCl$_3$, ppm): 8.01 (d, 1H), 7.42 (brs, 1H), 7.36 (d, 1H), 7.25-7.14 (m, 6H), 7.04 (d, 1H), 6.97 (d, 1H), 6.09 (t, 1H), 4.49 (d, 2H), 2.17 (s, 3H).

ES-MS (M+1): 505.0; (M+23): 527.0.

EXAMPLE 41 Preparation of Compound 41

1-((4-bromo-5-(5-bromoselenophen-2-yl)-1-(2,4-dichlorophenyl)-1H-pyrazol-3-yl)methyl)-3-propylurea Compound 41 was prepared in a manner similar to that described in Example 39 except that, in the last step, isocyanatocyclohexane was replaced with isocyanatopropane.

$^1$H-NMR (CDCl$_3$, ppm): 7.52 (d, 1H), 7.37 (d, 1H), 7.35 (s, 1H), 7.15 (d, 1H), 6.98 (d, 1H), 5.01 (s, 1H), 4.67 (s, 1H), 4.45 (d, 2H), 3.16-3.14 (m, 2H), 1.52-1.46 (m, 2H), 0.88 (t, 3H).

ES-MS (M+1): 612.8; (M+23): 634.8.

EXAMPLE 42 Preparation of Compound 42

1-((4-bromo-5-(5-bromoselenophen-2-yl)-1-(2,4-dichlorophenyl)-1H-pyrazol-3-yl)methyl)-3-cyclohexylthiourea Compound 42 was prepared in a manner similar to that described in Example 39 except that, in the last step, Intermediate VIII was treated with isothiocyanatocyclo-hexane (15 µL, 0.10 mmol) to give compound 42 as a white solid (45 mg, 75%).

$^1$H-NMR (CDCl$_3$, ppm): 7.52 (d, 1H), 7.38-7.29 (m, 2H), 7.14 (d, 1H), 6.98 (d, 1H), 4.62 (s, 2H), 1.94-1.65 (m, 11H).

ES-MS (M+23): 690.8.

EXAMPLE 43 Preparation of Compound 43

1-[1-(2,4-dichlorophenyl)-4-methyl-5-selenophen-2-yl-1H-pyrazol-3-ylmethyl]-3-phenyl-thiourea Compound 43 was prepared in a manner similar to that described in Example 40 except that, in the last step, isocyanatocyclohexane was replaced with isothiocyanatobenzene.

$^1$H-NMR (CDCl$_3$, ppm): 8.03 (d, 1H), 7.44 (d, 1H), 7.36-7.19 (m, 8H), 7.06 (d, 1H), 7.01 (brs, 1H), 4.90 (brs, 2H), 2.20 (s, 3H).

ES-MS (M+23): 543.0.

EXAMPLE 44 Preparation of Compound 44

N-((4-bromo-5-(5-bromoselenophen-2-yl)-1-(2,4-dichlorophenyl)-1H-pyrazol-3-yl)methyl)cyclohexanecarboxamide To a magnetically stirred solution of Intermediate VIII (50 mg, 0.09 mmol) in dichloromethan were added triethylamine (15 µL, 0.10 mmol) and cyclohexanecarbonyl chloride (18 µL, 0.12 mmol). After the mixture was stirred at room temperature for 8 hours, the reaction was quenched with water. The aqueous layer was separated and extracted with dichloromethan (2×10 mL). The combined extracts were washed with brine, dried over anhydrous sodium sulfate, filtered, and concentrated to give a crude product, which was purified with flash column chromatography on silica gel with n-hexane/ethyl acetate (3:1) to give compound 44 as a white solid (46 mg, 80%).

$^1$H-NMR (CDCl$_3$, ppm): 7.53 (d, 1H), 7.39 (d, 1H), 7.38 (s, 1H), 7.16 (d, 1H), 7.00 (d, 1H), 6.10 (brs, 1H), 4.55 (d, 2H), 2.16 (dt, 1H), 1.96-1.22 (m, 10H).

ES-MS (M+1): 637.8.

EXAMPLE 45 Preparation of Compound 45

N-((4-bromo-5-(5-bromoselenophen-2-yl)-1-(2,4-dichlorophenyl)-1H-pyrazol-3-yl)methyl)cyclopentanecarboxamide Compound 45 was prepared in a manner similar to that described in Example 44 except that Intermediate VIII was treated with triethylamine (15 µL, 0.10 mmol) and cyclopentanecarbonyl chloride (16 µL, 0.12 mmol) to give compound 45 as a white solid (41 mg, 73%).

$^1$H-NMR (CDCl$_3$, ppm): 7.49 (d, 1H), 7.35 (s, 1H), 7.34 (d, 1H), 7.12 (d, 1H), 6.96 (d, 1H) 6.12 (brs, 1H), 4.52 (d, 2H), 2.58-2.53 (m, 1H), 1.90-1.50 (m, 8H).

ES-MS (M+1): 623.8.

EXAMPLE 46 In Vitro Assays

The affinity of 45 test compounds of this invention toward CB1 and CB2 receptors was determined by competitive radioligand binding in vitro assays. This method differentiates the binding strength between compounds by their abilities in displacing a receptor-specific radioactive ligand. Compounds with higher affinity than the radioactive ligand displace the ligand and bind to the receptors, while compounds with no affinity or lower affinity than the radioactive ligand do not. The readings of the radioactivity retained allow further analysis of receptor binding, and assist in predictions of the pharmacological activities of the test compounds.

In the assays, brain and spleen extracts from male Sprague-Dawley rats were respectively utilized as the source of CB1 and CB2 receptors. Male Sprague-Dawley rats weighing 175~200 g were used and housed under standard stalling conditions with food and water available ad libitum. The animals were sacrificed by cervical dislocation. Brain with cerebellum were excluded and spleen were dissected from the animals. The separated brain and spleen tissues were respectively homogenized by Polytron Homogenizers in 10 volumes of ice-cold buffer A (50 mM Tris, 5 mM MgCl$_2$, 2.5 mM EDTA, pH 7.4, 10% sucrose) with protease inhibitors. The homogenate was centrifuged for 15 minutes at 2,000×g at 4° C. The resultant supernatant was centrifuged again for 30 minutes at 43,000×g at 4° C. The final pellet was re-suspended in buffer A and stored at −80° C. The protein concentration of the purified membrane was determined by the Bradford method as described by the manual provided by Bio-Rad Laboratories, Inc., Hercules, Calif.

During the receptor binding experiments, 0.2~8 µg of a membrane was incubated with 0.75 nM [$^3$H]CP55,940 and a test compound in an incubation buffer (50 mM Tris-HCl, 5 mM MgCl$_2$, 1 mM EDTA, 0.3% BSA, pH 7.4). The non-specific binding was determined by using 1 µM of CP55,940. The mixture was incubated for 1.5 hours at 30° C. in Multi-screen microplates (Millipore, Billerica, Mass.). At the completion of the incubation, the reaction was terminated by Manifold filtration and washed with ice-cold wash buffer (50 mM Tris, pH 7.4, 0.25% BSA) four times. The radioactivity bound to the filters was measured by Topcount (Perkin Elmer Inc.). IC$_{50}$ values were calculated based on the concentration of the test compound required to inhibit 50% of the binding of [$^3$H]CP55,940.

The efficacy of each test compound was determined by DELFIA GTP-binding kit (Perkin Elmer Inc., Boston, Mass.). The DELFIA GTP-binding assay is a time-resolved fluorometric assay based on GDP-GTP exchange on G-protein subunits followed by activation of a G protein-coupled receptor by its agonists. Eu-GTP was used in this assay to allow monitoring of agonist-dependent activation of G-protein. Note that stimulation of CB1 receptor by CP55,940 leads to the replacement of GDP by GTP on the α-subunit of G-protein. The resultant GTP-Gα complex represents the activated form of G-protein. Eu-GTP, a non-hydrolysable analogue of GTP, can be used to quantify the amount of activated G-protein (Peltonen et al., Eur. J. Pharmacol. (1998) 355:275).

Plasma membrane of human CB1-expressing HEK293 cells was re-suspended in an assay buffer (50 mM HEPES, pH 7.4, 100 mM NaCl, 100 µg/mL saponin, 5 mM $MgCl_2$, 2 µM GDP, 0.5% BSA). An aliquot (4 µg protein/well) was added to each well of an AcroPlate (Pall Life Sciences, Ann Arbor, Mich.). After the addition of a tested compound (various concentrations in 0.1% DMSO) and CP55,940 (20 nM in the assay buffer), the assay plate was incubated in the dark at 30° C. with slow shaking for 60 minutes. Eu-GTP was added to each well and the plate was incubated for another 35 minutes at 30° C. in the dark. The assay was terminated by washing the plate four times with a wash solution provided in the assay kit. Binding of the Eu-GTP was determined based on the fluorescence signal from a Victor 2 multi-label reader. The $IC_{50}$ value (i.e., 50% inhibition of CP55,940-stimulated Eu-GTP binding) for each test compound was determined by a concentration-response curve using nonlinear regression (Prism; GraphPad, San Diego, Calif.).

All of the test compounds showed $IC_{50}$ values lower than 10 µM in the CB1 receptor binding assays. More specifically, 32 of the test compounds showed $IC_{50}$ values toward CB1 receptor lower than 1 µM. Among them, 15 showed $IC_{50}$ values between 0.005 and 0.1 µM. Further, all of the test compounds showed $IC_{50}$ values between 0.2 and 20 µM in the CB2 receptor binding assays. The Eu-GTP binding assays were also conducted for all compounds toward CB1 receptors, and the results were comparable to those obtained from the above-mentioned CB1 radioligand binding assays.

OTHER EMBODIMENTS

All of the features disclosed in this specification may be combined in any combination. Each feature disclosed in this specification may be replaced by an alternative feature serving the same, equivalent, or similar purpose. Thus, unless expressly stated otherwise, each feature disclosed is only an example of a generic series of equivalent or similar features.

From the above description, one skilled in the art can easily ascertain the essential characteristics of the present invention, and without departing from the spirit and scope thereof, can make various changes and modifications of the invention to adapt it to various usages and conditions. Thus, other embodiments are also within the scope of the following claims.

What is claimed is:

1. A compound of formula (I):

(I)

wherein $R_1$ is $C_3$-$C_{20}$ cycloalkyl, $C_3$-$C_{20}$ cycloalkenyl, $C_1$-$C_{20}$ heterocycloalkyl, $C_1$-$C_{20}$ heterocycloalkenyl, aryl, or heteroaryl;

$R_2$ is $C(O)NR_aR_b$, in which each of $R_a$ and $R_b$, independently, is H, $C_1$-$C_{10}$ alkyl, $C_3$-$C_{20}$ cycloalkyl, $C_1$-$C_{20}$ heterocycloalkyl, aryl, or heteroaryl; and each of $R_3$, $R_4$, $R_5$, and $R_6$, independently, is H, halo, $C_1$-$C_{10}$ alkyl, $C_2$-$C_{10}$ alkenyl, $C_2$-$C_{10}$ alkynyl, $C_3$-$C_{20}$ cycloalkyl, $C_3$-$C_{20}$ cycloalkenyl, $C_1$-$C_{20}$ heterocycloalkyl, $C_1$-$C_{20}$ heterocycloalkenyl, aryl, or heteroaryl.

2. The compound of claim 1, wherein $R_1$ is aryl substituted with halo.

3. The compound of claim 2, wherein $R_1$ is 2,4-dichlorophenyl.

4. The compound of claim 3, wherein $R_2$ is $C(O)NR_aR_b$, in which $R_a$ is methyl substituted with 6,6-dimethylbicyclo[3.1.1]heptyl, ethyl substituted with admantyl or cyclohexenyl, hexyl, nonyl, cyclopentyl, cyclohexyl, cycloheptyl, pyridyl, morpholinyl, octahydrocyclopentapyrrolyl, or tetrahydronaphthyl; and $R_b$ is H.

5. The compound of claim 4, wherein the compound is one of compounds 1, 3-17, 19-24, 26-29, and 31-33.

6. A method for treating a cannabinoid-receptor mediated disorder, comprising administering to a subject in need thereof an effective amount of a compound of formula (I):

(I)

wherein $R_1$ is $C_3$-$C_{20}$ cycloalkyl, $C_3$-$C_{20}$ cycloalkenyl, $C_1$-$C_{20}$ heterocycloalkyl, $C_1$-$C_{20}$ heterocycloalkenyl, aryl, or heteroaryl;

$R_2$ is $C(O)NR_aR_b$, in which each of $R_a$ and $R_b$, independently, is H, $C_1$-$C_{10}$ alkyl, $C_3$-$C_{20}$ cycloalkyl, $C_1$-$C_{20}$ heterocycloalkyl, aryl, or heteroaryl; and each of $R_3$, $R_4$, $R_5$, and $R_6$, independently, is H, halo, $C_1$-$C_{10}$ alkyl, $C_2$-$C_{10}$ alkenyl, $C_2$-$C_{10}$ alkynyl, $C_3$-$C_{20}$ cycloalkyl, $C_3$-$C_{20}$ cycloalkenyl, $C_1$-$C_{20}$ heterocycloalkyl, $C_1$-$C_{20}$ heterocycloalkenyl, aryl, or heteroaryl.

7. The method of claim 6, wherein $R_1$ is aryl substituted with halo.

8. The method of claim 7, wherein $R_1$ is 2,4-dichlorophenyl.

9. The method of claim 8, wherein $R_2$ is $C(O)NR_aR_b$, in which $R_a$ is methyl substituted with 6,6-dimethylbicyclo[3.1.1]heptyl, ethyl substituted with admantyl or cyclohexenyl, hexyl, nonyl, cyclopentyl, cyclohexyl, cycloheptyl, pyridyl, morpholinyl, octahydrocyclopentapyrrolyl, or tetrahydronaphthyl; and $R_b$ is H.

10. The method of claim 6, wherein the cannabinoid-receptor mediated disorder is obesity, metabolic syndrome, substance addiction, or neuropathic pain.

* * * * *